(12) United States Patent
Wang et al.

(10) Patent No.: US 11,122,982 B2
(45) Date of Patent: Sep. 21, 2021

(54) FLEXIBLE EPIDERMAL MULTIMODAL HEALTH MONITOR

(71) Applicant: The Regents of the University of California, Oakland, CA (US)

(72) Inventors: Joseph Wang, San Diego, CA (US); Patrick Mercier, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 27 days.

(21) Appl. No.: 16/090,083

(22) PCT Filed: Apr. 3, 2017

(86) PCT No.: PCT/US2017/025798
§ 371 (c)(1),
(2) Date: Sep. 28, 2018

(87) PCT Pub. No.: WO2017/173462
PCT Pub. Date: Oct. 5, 2017

(65) Prior Publication Data
US 2019/0117083 A1    Apr. 25, 2019

Related U.S. Application Data

(60) Provisional application No. 62/316,822, filed on Apr. 1, 2016.

(51) Int. Cl.
*A61B 5/02*   (2006.01)
*A61B 5/0205* (2006.01)
(Continued)

(52) U.S. Cl.
CPC ............ *A61B 5/0205* (2013.01); *A61B 5/053* (2013.01); *A61B 5/6833* (2013.01);
(Continued)

(58) Field of Classification Search
CPC .............. A61B 5/14532; A61B 5/1486; A61B 5/14865
See application file for complete search history.

(56) References Cited

U.S. PATENT DOCUMENTS 6,587,705 B1   7/2003   Kim et al.
7,998,666 B2   8/2011   Stiene et al.
(Continued)

OTHER PUBLICATIONS

Bandodkar, A.J. et al., Non-invasive wearable electrochemical sensors: a review. Trends Biotechnol. 32, 363-371 (2014).
(Continued)

*Primary Examiner* — Michael J D Abreu
(74) *Attorney, Agent, or Firm* — Perkins Coie LLP

(57) ABSTRACT

Methods, systems, and devices are disclosed for wearable, real-time multimodal sensing of electrochemical and electrophysiological and/or physical parameters of a user. In some aspects, a multimodal sensor device includes a flexible substrate; an electrochemical sensor disposed on the substrate and including electrochemical sensing electrodes operable to measure an electrical signal corresponding to a reaction including a chemical substance via an electrochemical sensing electrode and an analyte at the electrochemical sensor; and an electrophysiological sensor including two or more electrodes disposed on the substrate to acquire an electrophysiological signal of the user, such that when the multimodal sensor device is electrically coupled to an electronics unit and adhered to the user, the device is operable to simultaneously monitor an electrochemical parameter and an electrophysiological parameter of the user.

23 Claims, 13 Drawing Sheets

(51) Int. Cl.
| | |
|---|---|
| A61B 5/053 | (2021.01) |
| A61B 5/00 | (2006.01) |
| A61B 5/1468 | (2006.01) |
| A61B 5/259 | (2021.01) |
| A61B 5/282 | (2021.01) |
| A61B 5/318 | (2021.01) |
| A61B 5/08 | (2006.01) |
| A61B 5/145 | (2006.01) |
| A61B 5/1486 | (2006.01) |

(52) U.S. Cl.
CPC ......... *A61B 5/02055* (2013.01); *A61B 5/0816* (2013.01); *A61B 5/1468* (2013.01); *A61B 5/1486* (2013.01); *A61B 5/14532* (2013.01); *A61B 5/259* (2021.01); *A61B 5/282* (2021.01); *A61B 5/318* (2021.01); *A61B 2562/066* (2013.01); *A61B 2562/164* (2013.01)

(56) References Cited

U.S. PATENT DOCUMENTS

| | | | |
|---|---|---|---|
| 8,463,351 | B2 | 6/2013 | Say et al. |
| 8,565,849 | B2 | 10/2013 | Kamath et al. |
| 9,502,730 | B2 | 11/2016 | Wang et al. |
| 10,595,759 | B2 | 3/2020 | Wang et al. |
| 2008/0091089 | A1 | 4/2008 | Guillory et al. |
| 2015/0126834 | A1 | 5/2015 | Wang et al. |
| 2015/0351690 | A1 | 12/2015 | Toth et al. |
| 2017/0325724 | A1* | 11/2017 | Wang .................. A61B 5/6833 |

OTHER PUBLICATIONS

Bandodkar, A.J. et al., Tattoo-based potentiometric ion-selective sensors for epidermal pH monitoring. Analyst 138, 123-8 (2013).
Bandodkar, A.J. et al., Tattoo-based noninvasive glucose monitoring: a proof-of-concept study. Anal. Chem. 87, 394-8 (2015).
Bandodkar, A.J. et al., "Epidermal tattoo potentiometric sodium sensors with wireless signal transduction for continuous non-invasive sweat monitoring.," Biosensors & Bioelectronics, vol. 54, pp. 603-609, May 2014.
Bandodkar, A.J. et al., "Solid-state Forensic Finger sensor for integrated sampling and detection of gunshot residue and explosives: towards 'Lab-on-a-finger'.," Analyst, vol. 138, No. 18, pp. 5288-5295, Oct. 2013.
Bandyopadhyay, S. et al., "A 1.1nW Energy Harvesting System with 544pW Quiescent Power for Next Generation Implants," in IEEE ISSCC Dig. Tech. Papers, 2014, pp. 396-397.
Bembnowicz, P. et al., "Wearable electronic sensor for potentiometric and amperometric measurements," IEEE International Conference on Body Sensor Networks, No. 1, pp. 1-5, May 2013.
Biagi, S. et al., Simultaneous determination of lactate and pyruvate in human sweat using reversed-phase high-performance liquid chromatography: a noninvasive approach. Biomed. Chromatogr. 26, 1408-1415 (2012).
Bian, Z.G. et al., Thermal analysis of ultrathin, compliant sensors for characterization of the human skin. Rsc Adv. 4, 5694-5697 (2014).
Buono, M.J. et al., The relationship between exercise intensity and the sweat lactate excretion rate. J. Physiol. Sci. 60, 103-107 (2010).
Butler, J. et al., Worsening heart failure hospitalization epidemic we do not know how to prevent and we do not know how to treat! Journal of the American College of Cardiology 52, 435-7 (2008).
Cai, J. et al., "Flexible Thick-Film Electrochemical Sensors: Impact of Mechanical Bending and Stress on the Electrochemical Behavior.," Sensors and Actuators B: Chemical, vol. 137, No. 1, pp. 379-385, Mar. 2009.
Chi, Y.M. et al., Non-contact Low Power EEG/ECG Electrode for High Density Wearable Biopotential Sensor Networks. 2009 Sixth Int. Work. Wearable Implant. Body Sens. Networks 246-250 (2009).

Chiarugi, F. et al., Measurement of heart rate and respiratory rate using a textile-based wearable device in heart failure patients. 2008 Comput. Cardiol. 35, 901-904 (2008).
Childs, P.R.N. et al., "Review of temperature measurement," Review of Scientific Instruments, vol. 71, No. 8, p. 2959, 2000.
Chuang, M.C. et al., Flexible thick-film glucose biosensor: Influence of mechanical bending on the performance. Talanta 81, 15-19 (2010).
Cong, P. et al., Wireless batteryless implantable blood pressure monitoring microsystem for small laboratory animals. IEEE Sens. J. 10, 243-254 (2010).
Daly, D.C. et al., "A Pulsed UWB Receiver SoC for Insect Motion Control," IEEE Journal of Solid-State Circuits, vol. 45, No. 1, pp. 153-166, Jan. 2010.
Di Rienzo, M. et al., Textile technology for the vital signs monitoring in telemedicine and extreme environments. IEEE Trans. Inf. Technol. Biomed. 14, 711-717 (2010).
Falk, B. et al., Sweat lactate in exercising children and adolescents of varying physical maturity. J. Appl. Physiol. 71, 1735-1740 (1991).
Fletcher, P.C. et al., "Risk Factors for Falling Among Community-Based Seniors Using Home Care Services," The Journals of Gerontology Series A: Biological Sciences and Medical Sciences, vol. 57, No. 8, pp. M504-M510, Aug. 2002.
Gargiulo, G. et al., A mobile EEG system with dry electrodes. 2008 IEEE-BIOCAS Biomed. Circuits Syst. Conf. BIOCAS 2008 273-276 (2008).
Gore, A. et al., "A Multichannel Femtoampere-Sensitivity Potentiostat Array for Biosensing Applications," IEEE Transactions on Circuits and Systems I: Regular Papers, vol. 53, No. 11, pp. 2357-2363, 2006.
Green, J.M. et al., Sweat lactate response between males with high and low aerobic fitness. Eur. J. Appl. Physiol. 91, 1-6 (2004).
Guinovart, T. et al., "A potentiometric tattoo sensor for monitoring ammonium in sweat.," Analyst, vol. 138, No. 22, pp. 7031-7038, Dec. 2013.
Harrigan, R. et al., Electrocardiographic electrode misplacement, misconnection, and artifact. J. Emerg. Med. 43, 1038-1044 (2012).
Harrison, R.R. et al., "A Low-Power Low-Noise CMOS Amplifier for Neural Recording Applications," IEEE Journal of Solid-State Circuits, vol. 38, No. 6, pp. 958-965, 2003.
Hasegawa, Y. et al., Fabrication of a wearable fabric tactile sensor produced by artificial hollow fiber. J. Micromechanics Microengineering 18, 085014 (2008).
Havenith, G. et al., Male and female upper body sweat distribution during running measured with technical absorbents. Eur. J. Appl. Physiol. 104, 245-255 (2008).
Heidenreich, P.A. et al., Forecasting the future of cardiovascular disease in the United States: a policy statement from the American Heart Association. Circulation 123, 933-44 (2011).
Imani, S. et al., A Wearable Chemical-Electrophysiological Hybrid Biosensing System for Real-Time Health and Fitness Monitoring, Nature Communications, 2016, 7 pages.
Jeong, J.W. et al., Wearable Respiratory Rate Monitoring using Piezo-resistive Fabric Sensor. World Congr. Med. Phys. Biomed. Eng. 282-284 (2009).
Jia, W. et al., Electrochemical tattoo biosensors for real-time non-invasive lactate monitoring in human perspiration. Anal. Chem. 85, 6553-60 (2013).
Jia, W. et al., "Epidermal biofuel cells: energy harvesting from human perspiration.," Angewandte Chemie (International ed. in English), vol. 52, No. 28, pp. 7233-7236, Jul. 2013.
Jung, S. et al., Point-of-care temperature and respiration monitoring sensors for smart fabric applications. Smart Mater. Struct. 15, 1872-1876 (2006).
Karyakin, A., Prussian blue and its analogues: Electrochemistry and analytical applications. Electroanalysis 13, 813-819 (2001).
Kim, D.-H. et al., Flexible and Stretchable Electronics for Biointegrated Devices. Annu. Rev. Biomed. Eng. 14, 113-128 (2012).
Kim, D.-H. et al., Epidermal Electronics. Science 333, 838-844 (2011).
Kim, J. et al., Non-invasive mouthguard biosensor for continuous salivary monitoring of metabolites. Analyst 139, 1632-6 (2014).

(56) References Cited

OTHER PUBLICATIONS

Kim, J. et al., Wearable salivary uric acid mouthguard biosensor with integrated wireless electronics. Biosens. Bioelectron. 74, 1061-1068 (2015).
Kirwan, S.M. et al., Modifications of Poly(o-phenylenediamine) Permselective Layer on Pt—Ir for Biosensor Application in Neurochemical Monitoring, sensors, vol. (7), pp. 420-437, Apr. 12, 2007; p. 421, highlight.
Kjellmer, I., "The Role of Potassium Ions in Exercise Hyperaemia," Pharmacology, vol. 5, No. 1, pp. 56-60, 1961.
Kostis, J.B. et al., The effect of age on heart rate in subjects free of heart disease. Studies by ambulatory electrocardiography and maximal exercise stress test. Circulation 65, 141-145 (1982).
Lee, Y.-D. et al., Wireless sensor network based wearable smart shirt for ubiquitous health and activity monitoring. Sensors Actuators B Chem. 140, 390-395 (2009).
Lee, S.M. et al., Self-adhesive epidermal carbon nanotube electronics for tether-free long-term continuous recording of biosignals. Sci. Rep. 4, 1-9 (2014).
Lewenstam, A. et al., "Application of ion-selective electrodes in clinical analysis," Electroanalysis, vol. 3, No. 8, pp. 727-734, Oct. 1991.
Liao, Y.-T. et al., "A 3-uW CMOS Glucose Sensor for Wireless Contact-Lens Tear Glucose Monitoring," IEEE Journal of Solid-State Circuits, vol. 47, pp. 335-344, 2012.
Lofhede, J. et al., Textile electrodes for EEG recording—a pilot study. Sensors (Basel). 12, 16907-19 (2012).
Lorussi, F. et al., Strain sensing fabric for hand posture and gesture monitoring. IEEE Trans. Inf. Technol. Biomed. 9, 372-81 (2005).
Lorussi, F. et al., Wearable, redundant fabric-based sensor arrays for reconstruction of body segment posture. IEEE Sens. J. 4, 807-818 (2004).
Zhang, F. et al., "Design of ultra-low power biopotential amplifiers for biosignal acquisition applications," IEEE Trans. Biomedical Circuits and Systems, vol. 6, No. 4, pp. 344-355, 2012.
International Search Report and Written Opinion for PCT Application No. PCT/US2017/025798, dated Jul. 6, 2017, 18 pages.
Lu, N. et al., "Highly Sensitive Skin-Mountable Strain Gauges Based Entirely on Elastomers," Advanced Functional Materials, vol. 22, No. 19, pp. 4044-4050, Oct. 2012.
Lykken, D.T., "The GSR in the detection of guilt.," Journal of Applied Psychology, vol. 43, No. 6, pp. 385-388, 1959.
MacDonald, J.B., "The role of drugs in falls in the elderly.," Clinics in Geriatric Medicine, vol. 1, No. 3, pp. 621-636, Aug. 1985.
Mattmann, C. et al., Sensor for Measuring Strain in Textile. Sensors 8, 3719-3732 (2008).
Medicare Payment Advisory Commission. Report to the Congress: Reforming the Delivery system. (2008). at <http://www.medpac.gov/documents/Jun08_EntireReport.pdf>.
Mercier, P.P. et al., "Energy extraction from the biologic battery in the inner ear," Nature Biotechnology, vol. 30, No. 12, pp. 1240-1243, Dec. 2012.
Mercier, P.P. et al., "Rapid Wireless Capacitor Charging Using a Multi-Tapped Inductively-Coupled Secondary Coil," IEEE Transactions on Circuits and Systems I, vol. 60, No. 9, pp. 2263-2272, Sep. 2013.
Mercier, P.P. et al., "A Supply-Rail-Coupled eTextiles Transceiver for Body-Area Networks," IEEE Journal of Solid-State Circuits, vol. 46, No. 6, pp. 1284-1295, Jun. 2011.
Mercier, P.P. et al., "A 78 pW 1 b/s 2.4 GHz Radio Transmitter for Near-Zero-Power Sensing Applications," in Proc. IEEE European Solid-State Circuits Conference, 2013, pp. 133-136.
Merritt, C.R. et al, Textile-based capacitive sensors for respiration monitoring. IEEE Sens. J. 9, 71-78 (2009).
Muehlsteff, J. et al,. Continuous cuff-less blood pressure monitoring based on the pulse arrival time approach: the impact of posture. Conf. Proc. IEEE Eng. Med. Biol. Soc. 2008, 1691-1694 (2008).
Murphy, S. et al., Deaths: Final data for 2010. Natl. Vital Stat. Rep. 61, (2013).

Nemati, E. et al., "A wireless wearable ECG sensor for long-term applications," IEEE Communications Magazine, vol. 50, No. 1, pp. 36-43, Jan. 2012.
Northridge, M.E. et al., "Home hazards and falls in the elderly: the role of health and functional status.," American Journal of Public Health, vol. 85, No. 4, pp. 509-515, Apr. 1995.
Paidimarri, A. et al., "A 2.4 GHz Multi-Channel FBAR-based Transmitter With an Integrated Pulse-Shaping Power Amplifier," IEEE Journal of Solid-State Circuits, vol. 48, No. 4, pp. 1042-1054, Apr. 2013.
Pandian, P.S. et al,. Smart Vest: Wearable multi-parameter remote physiological monitoring system. Med. Eng. Phys. 30, 466-477 (2008).
Patterson, M.J. et al., Variations in regional sweat composition in normal human males. Exp. Physiol. 85, 869-875 (2000).
Pilardeau, P.A. et al., Effect of different work-loads on sweat production and composition in man. Sport. Med. Phys. Fit. 28, 247-252 (1988).
Pillardeau, P. et al., Secretion of Eccrine Sweat Glands During Exercise. Brit. J. Sport. Med. 118-121 (1979).
Polliack et al., Sweat analysis following pressure ischaemia in a group of debilitated subjects. J. Rehabil. Res. Dev. 34, 303-308 (1997).
Pollock, M.L. et al., Resistance Exercise in Individuals With and Without Cardiovascular Disease. Circulation 101, 828-833 (2000).
Rantanen, T. et al., "Disability, physical activity, and muscle strength in older women: The women's health and aging study," Archives of Physical Medicine and Rehabilitation, vol. 80, No. 2, pp. 130-135, Feb. 1999.
Rittweger, J. et al., Acute physiological effects of exhaustive whole-body vibration exercise in man. Clin. Physiol. 20, 134-142 (2000).
Rosendal, L. et al., "Interstitial muscle lactate, pyruvate and potassium dynamics in the trapezius muscle during repetitive low-force arm movements, measured with microdialysis.," Acta Physiologica, vol. 182, No. 4, pp. 379-388, Dec. 2004.
Ross, J.S. et al., Recent national trends in readmission rates after heart failure hospitalization. Circulation. Heart failure 3, 97-103 (2010).
Rossat, A. et al., "Association between benzodiazepines and recurrent falls: A cross-sectional elderly population-based study," The Journal of Nutrition, Health & Aging, vol. 15, No. 1, pp. 72-77, Feb. 2011.
Rothmaier, M. et al,. Photonic textiles for pulse oximetry. Opt. Express 16, 12973-12986 (2008).
Rovira, C. et al., Integration of textile-based sensors and Shimmer for breathing rate and volume measurement. 2011 5th Int. Conf. Pervasive Comput. Technol. Healthc. Work. m, 238-241 (2011).
Salem, L. et al., "An 85%-Efficiency Fully-Integrated 15-Ratio Recursive Switched-Capacitor DC-DC Converter With 0.1-2.2V Output Voltage Range," in IEEE ISSCC Dig. Tech. Papers, 2014, pp. 88-89.
Selmer, R.M. et al., Cost and health consequences of reducing the population intake of salt. Journal of Epidemiology and Community Health 54, 697-702 (2000).
Somjen, G.G. et al., "Potassium and calcium concentrations in interstitial fluid of hippocampal formation during paroxysmal responses," J Neurophysiol, vol. 53, No. 4, pp. 1098-1108, Apr. 1985.
Son, D. et al., Multifunctional wearable devices for diagnosis and therapy of movement disorders. Nat. Nanotechnol. 9, 397-404 (2014).
Soper, S. et al., Point-of-care biosensor systems for cancer diagnostics/prognostics. Biosens. Bioelectron. 21, 1932-1942 (2006).
Speechley, M. et al., "Falls and injuries in frail and vigorous community elderly persons.," Journal of the American Geriatrics Society, vol. 39, No. 1, pp. 46-52, Jan. 1991.
Stevens, J., "A CDC compendium of effective fall interventions: what works for community-dwelling older adults. Atlanta, GA: Centers for Disease Control and Prevention, National Center for Injury Prevention and Control," 2010. [Online]. Available: http://www.cdc.gov/homeandrecreationalsafety/Falls/compendium.html. [Accessed: Feb. 5, 2014].

(56) References Cited

OTHER PUBLICATIONS

Su, H. et al., "A Non-contact Biopotential Sensing System With Motion Artifact Suppression," in Proc. IEEE International Conference on Communications, Circuits, and Systems, 2013.

Tatterson, A.J. et al., Effects of heat stress on physiological responses and exercise performance in elite cyclists. J. Sci. Med. Sport 3, 186-193 (2000).

Tudos, J. et al., Trends in miniaturized total analysis systems for point-of-care testing in clinical chemistry. Lab Chip 1, 83-95 (2001).

Wang, J., Amperometric biosensors for clinical and therapeutic drug monitoring: a review. J. Pharm. Biomed. Anal. 19, 47-53 (1999).

Wang, J., "Portable electrochemical systems," Trends in Analytical Chemistry, vol. 21, No. 4, pp. 226-232, Apr. 2002.

Wasserman, K. et al., Interaction mechanisms of physiological during exercise. J. Appl. Physiol. 22, 71-85 (1967).

Welch, J. et al., Early detection of the deteriorating patient: the case for a multi-parameter patient-worn monitor. Biomedical instrumentation & technology / Association for the Advancement of Medical Instrumentation Suppl, 57-64 (2012).

Wiens, J. et al., "A study in transfer learning: leveraging data from multiple hospitals to enhance hospital-specific predictions.," Journal of the American Medical Informatics Association, Jan. 2014.

Wikipedia, Electroencephalography, Dec. 29, 2015; p. 1/27, para 1; Retrieved on May 31, 2017, from <https://en.wikipedia.org/wikVElectroencephalography>.

Wikipedia, Bluetooth Low Energy, Dec. 30, 2015; p. 1/10, para 1; Retrieved on May 31, 2017, from <https://en.wikipedia.org/wikVBluetooth_Low_Energy>.

Windmiller, J.R. et al., Wearable Electrochemical Sensors and Biosensors: A Review. Electroanalysis 25, 29-46 (2013).

Windmiller, J.R. et al., "Electrochemical sensing based on printable temporary transfer tattoos.," Chemical Communications, vol. 48, No. 54, pp. 6794-6796, Jul. 2012.

Winokur, E.S. et al., "A wearable cardiac monitor for long-term data acquisition and analysis.," IEEE Transactions on BioMedical Engineering, vol. 60, No. 1, pp. 189-192, Jan. 2013.

Yarasheski, K.E. et al., Acute effects of resistance exercise on muscle protein synthesis rate in young and elderly men and women. Am. J. Physiol. 265, E210-E214 (1993).

Yoo, J. et al., "A wearable ECG acquisition system with compact planar-fashionable circuit board-based shirt.," IEEE Transactions on Information Technology in Biomedicine, vol. 13, No. 6, pp. 897-902, Nov. 2009.

\* cited by examiner

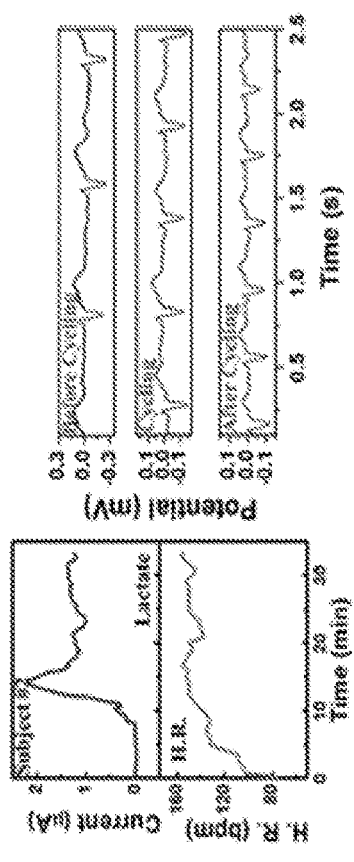
FIG. 6A
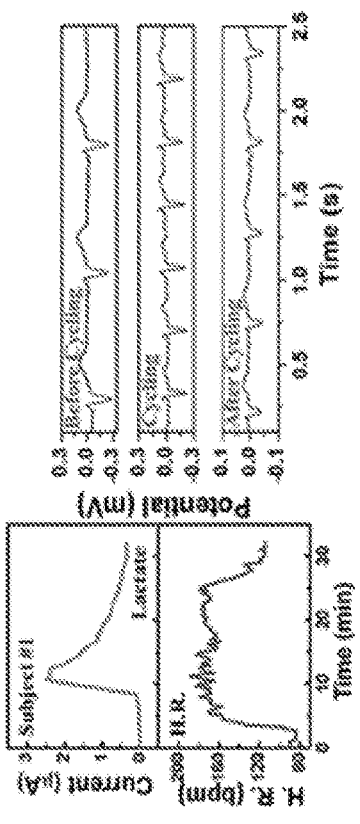
FIG. 6B
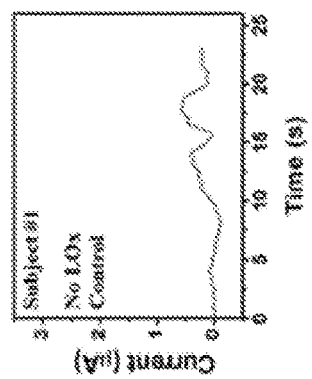
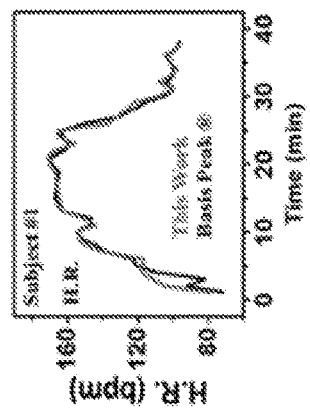
FIG. 6D
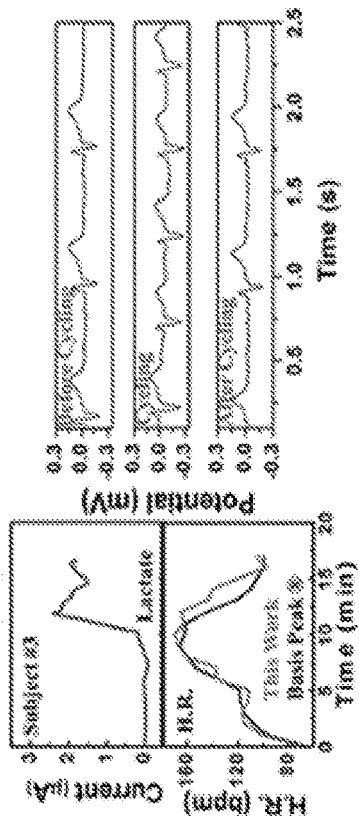
FIG. 6C
FIG. 6E

FLEXIBLE EPIDERMAL MULTIMODAL HEALTH MONITOR

CROSS-REFERENCE TO RELATED APPLICATIONS

This patent document is a 371 National Phase Application of PCT Application No. PCT/US2017/025798 entitled "FLEXIBLE EPIDERMAL MULTIMODAL HEALTH MONITOR" filed on Apr. 3, 2017, which claims priorities to and benefits of U.S. Provisional Patent Application No. 62/316,822 entitled "FLEXIBLE EPIDERMAL MULTIMODAL HEALTH MONITOR" filed on Apr. 1, 2016. The entire contents of the aforementioned patent applications are incorporated by reference as part of the disclosure of this patent document.

STATEMENT REGARDING FEDERALLY SPONSORED RESEARCH OR DEVELOPMENT

This invention was made with government support under EB019698 awarded by the National Institutes of Health. The government has certain rights in the invention.

TECHNICAL FIELD

This patent document relates to systems, devices, and processes that use biosensing technologies for real-time health and fitness monitoring.

BACKGROUND

Sensors based on electrochemical processes can be used to detect a chemical substance or a biological substance (e.g., an organism) by using a transducing element to convert a detection event into a signal for processing and/or display. Biosensors can use biological materials as the biologically sensitive component, e.g., such as biomolecules including enzymes, antibodies, nucleic acids, etc., as well as living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by optical, electronic or other means. For example, the transduction mechanisms can include physicochemical, electrochemical, optical, piezoelectric, as well as other transduction means.

SUMMARY

Techniques, systems, and devices are disclosed for implementing a real-time, non-invasive monitoring of multiple health parameters, including but not limited to electrochemical, electrophysiological, and physical parameters.

In some aspects, a multimodal sensor device includes a flexible substrate including an electrically insulative material and structured to adhere to a user; an electrochemical sensor including a first electrode disposed on the substrate, in which the first electrode includes a surface including a chemical substance that includes a catalyst or a reactant corresponding to an analyte in a fluid, and a second electrode disposed on the substrate separated from the first electrode, the first and second electrodes operable to measure an electrical signal corresponding to a redox reaction including the chemical substance and analyte at the electrochemical sensor; and an electrophysiological sensor including two or more electrodes disposed on the substrate to acquire an electrophysiological signal of the user, in which, when the device is electrically coupled to an electronics unit and adhered to the user, the device is operable to simultaneously monitor an electrochemical parameter and an electrophysiological parameter of the user.

In some aspects, a multimodal health monitoring system includes a multimodal sensor device attachable to skin of a user and a wireless receiver device. The multimodal sensor device is structured to include a flexible substrate including an electrically insulative material and structured to adhere to the user, an electrochemical sensor including a first electrode disposed on the substrate, in which the first electrode includes a surface including a chemical substance that includes a catalyst or a reactant corresponding to an analyte in a fluid of the user, and a second electrode disposed on the substrate separated from the first electrode, the first and second electrodes operable to measure an electrical signal corresponding to a redox reaction including the chemical substance and analyte at the electrochemical sensor, an electrophysiological sensor including two or more electrodes disposed on the substrate and operable to acquire an electrophysiological signal of the user, and an electronics unit, including a signal conditioning circuit to amplify detected signals including the electrical signal measured by the electrochemical sensor and the electrophysiological signal acquired by the electrophysiological sensor, and a wireless communications unit to wirelessly transmit the amplified signals to an external device, in which the multimodal sensor device is operable to simultaneously monitor an electrochemical parameter and an electrophysiological parameter of the user. The wireless receiver device is operable to receive the wirelessly transmitted signals from the multimodal sensor device.

In some aspects, a method to simultaneously monitor an electrochemical parameter and an electrophysiological parameter of a user includes: detecting, at electrodes of an electrochemical sensor disposed on a flexible substrate adhered to skin of the user, a first electrical signal produced as a result of a redox reaction involving an analyte in a fluid of the user and a chemical substance coupled to an electrode of the electrochemical sensor; detecting, at electrodes of an electrophysiological sensor disposed on the flexible substrate adhered to the skin of the user, a second electrical signal associated with an electrophysiological signal of the user, in which the detecting the first electrical signal and the second electrical signal occurs simultaneously; amplifying, at an electronics unit, the first electrical signal detected by the electrochemical sensor and the second electrical signal detected by the electrophysiological sensor; and wirelessly transmitting, at the electronics unit, the first electrical signals and second electrical signal to an external device.

In some embodiments, a multimodal, real-time wearable health monitor device measures multiple physiological parameters including electrochemical parameters, electrophysiological parameters, and physical parameters simultaneously on a single platform. The device includes sensing techniques include amperometry for metabolite monitoring (e.g., glucose, lactate); potentiometry for electrolyte monitoring (e.g., K+, Na+, Cl—, pH); low-noise amplification for biopotential monitoring (e.g., ECG, EEG, EMG); and strain and temperature-induced resistivity changes for physical parameter monitoring (e.g., skin temperature via temperature-induced resistivity changes, respiration rate, strain, acceleration, etc.). For example, the device can be fabricated either within an epidermal temporary tattoo, a textiles patch, a band aid, or other flexible substrates. In some embodiments, electrolytes and metabolites are monitored in the wearer's perspiration. In some embodiments, electrolytes and metabolites are monitored in sub-dermal fluid using a reverse iontophoresis process.

In example embodiments include two sensing modalities of lactate monitoring and ECG monitoring, a three-electrode amperometric lactate biosensor and a bipolar ECG sensor co-fabricated on a flexible substrate can be mounted on the skin for real-time, continuous monitoring of chemical and electrophysiological health marker. For example, inclusion of chemical measurements can provide extremely useful insights into the performance level and health status of the individual not available from physical or electrophysiological sensors.

BRIEF DESCRIPTION OF THE DRAWINGS

FIGS. 6A-6E show data plots of example real-time, on-body evaluations of the example Chem-Phys hybrid patch showing the lactate levels and heart rate for human subjects.

DETAILED DESCRIPTION

Figure 1:
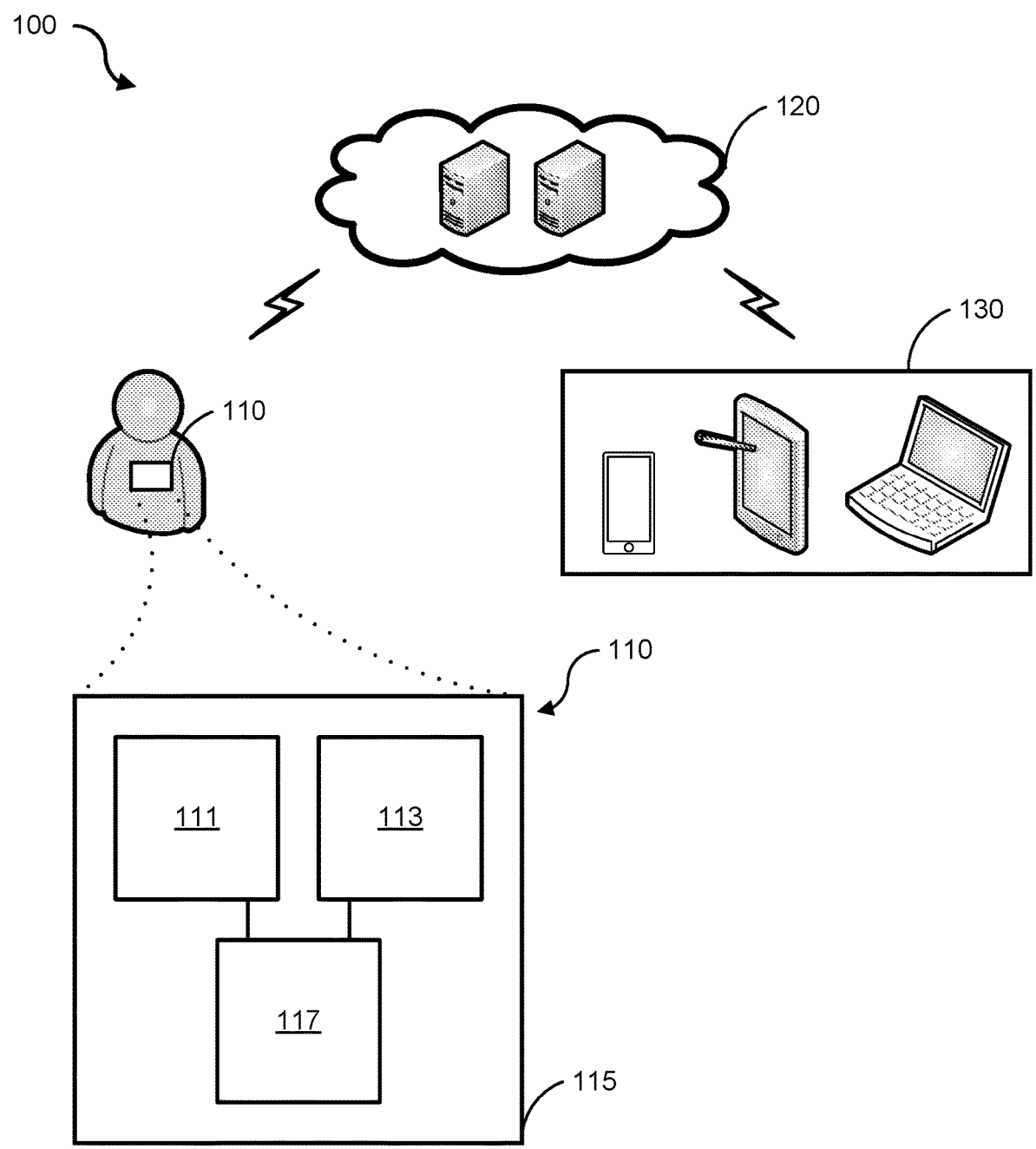
FIG. 1 shows a diagram of an example embodiment of a system for monitoring the health or fitness condition of a user wearing a multimodal sensor in accordance with the present technology.

Recent advances in hybrid fabrication techniques have enabled the design of wearable sensing devices in thin, conformal form factors that naturally comply with the smooth curvilinear geometry of human skin, thereby enabling intimate contact between the skin and the device necessary for robust physiological measurements. To date, conventional sensing platforms systems have targeted only a single measurement at a time, e.g., such as measuring only physical and electrophysiological parameters, significantly limiting the monitoring information and diagnostic opportunities. Current wearable devices that only measure heart rate, motion, or an electrophysiological parameter such as an electrocardiogram (ECG) provide an incomplete picture of the complex physiological changes taking place. As such, these conventional devices fail to comprehensively measure and assess a user's real-time health status or condition mainly due to limitations of the device platform in only capturing one or both of electrophysiology and physical parameter measurements.

To better understand the health of a subject, relevant biochemical measurements alongside electrophysiological and/or physical measurements can paint a more complete picture. For example, the human body undergoes complex physiological changes during physical activities such as exercise, and monitoring the physiologic effect of physical activity can be important for a wide variety of subjects, e.g., ranging from athletes to the elderly and patients. Inclusion of chemical measurements can provide extremely useful insights into the performance level and health status of the individual not available from physical or electrophysiological sensors. Currently, there is no existing device that monitors chemical parameters simultaneously with electrophysiological and/or physical parameters in real-time and in a non-invasive manner.

For example, flexible, wearable sensing devices can yield important information about the underlying physiology of a human subject for applications in real-time health and fitness monitoring. Despite significant progress in the fabrication of flexible biosensors that naturally comply with the epidermis, most designs measure only a small number of physical or electrophysiological parameters, and neglect the rich chemical information available from biomarkers.

Disclosed is a platform for a multimodal, real-time wearable health monitor. The multimodal, wearable sensors in accordance with the present technology integrate physiologically relevant sensing modalities into a single platform for continuous, simultaneous sensing of multiple, differing parameters, e.g., which are relevant for assessment of a wide range of conditions, diseases, health, and performance states.

In some embodiments of the disclosed multimodal, wearable sensor technology, a skin-worn wearable hybrid sensing device is disclosed that offers simultaneous real-time monitoring of a biochemical (e.g., lactate) and an electrophysiological signal (e.g., ECG), providing comprehensive fitness monitoring (e.g., more relevant data and enriched analysis than from physical or electrophysiological sensors alone). The two example sensing modalities are integrated on a single flexible substrate that attaches to a user's skin, e.g., in a form factor of a single epidermal patch. In this example embodiment, the electrochemical sensing module includes a three-electrode amperometric lactate biosensor, and the electrophysiological sensing module includes a bipolar ECG sensor, which are co-fabricated on the flexible substrate and able to be mounted on the skin. Example implementations using the example skin-worn lactate-ECG hybrid sensing device worn by human subjects reveal that physiochemistry and electrophysiology parameters can be measured simultaneously with negligible cross-talk, e.g., validating this class of hybrid sensing devices. In embodiments of the disclosed multimodal, wearable sensor technology, other sensing modalities can be integrated on the flexible substrate, e.g., including but not limited to, monitoring of respiration rate, heart rate, blood oxygenation, skin temperature, bodily motion, brain activity, and/or blood pressure.

FIG. 1 shows a diagram of an example embodiment of a system 100 for monitoring the health or fitness condition of a user wearing a multimodal sensor 110 in accordance with the present technology. The system 100 includes the multimodal sensor 110 wearable by a user over a region of the user's body to detect the desired parameters detectable by the multimodal sensor 110. In some embodiments, the system 100 includes a data processing system 120 in communication with the multimodal sensor 110.

The multimodal sensor 110 includes an electrochemical sensing module 111 and a second sensing module 113, e.g., including an electrophysiological sensor and/or a physical sensor, in which the electrochemical sensing module 111 and the second sensing module 113 are disposed on a flexible substrate 115. The multimodal sensor 110 includes an electronics unit 117 in communication with the electrochemical sensing module 111 and the electrophysiological and/or physical sensing module 113. The electronics unit 117 is disposed on the electronics unit 117. In some implementations, the electronics unit 117 can include or interface with a power supply unit, e.g., such as a battery, fuel cell or other power source, to supply power to various components of the multimodal sensor 110.

The substrate 115 includes a material that is mechanically flexible (e.g., bendable) to mechanically conform to the skin of the user. The material of the flexible substrate 115 can include an adhesive property to enable the multimodal sensor 110 to securely attach to the target region on the body of the user. In some implementations, the flexible substrate 115 allows for secure attachment, detachment and reattachment to the user's body. For example, flexible substrate 115 can include, but is not limited to, polymer, textile (e.g., polyester), or ceramic materials. In some implementations, for example, the flexible substrate 115 includes a temporary tattoo (e.g., of a paper material), a textiles patch, a band aid, or of other flexible substrate types. The flexible substrate 115 can be configured to have a thickness in a range of a few millimeters to tens of microns, e.g., such as a 50 µm thickness.

The electronics unit 117 can include electrical circuit elements (e.g., impedance elements, diodes, transistors, etc.) and/or electronic components (e.g., processor, analog-to-digital (A/D) and/or digital-to-analog (D/A) converters, memory, wireless transmitter/receiver, instrumentation electronics, etc.) to provide signal conditioning, signal and data processing, storage, and/or communication. For example, the electronics unit 117 can be configured to control the electrochemical analysis techniques to detect the target analyte by the electrochemical sensing module 111, e.g., including but not limited to chronoamperometry, chronopotentiometry, voltammetry, cyclic voltammetry, linear sweep electrochemical techniques, polarography, pulsed electrochemical analysis techniques, impedance spectroscopy, etc. Similarly, the electronics unit 117 can be configured to control data acquisition by the electrophysiological sensing module and/or physical sensing module.

In some implementations, the electronics unit 117 can include a signal conditioning unit 171, a transceiver unit 173, and a power supply 175. The signal conditioning unit 171 can include instrumentational amplifier(s) and filter(s) to condition the detected signal, e.g., improving signal-to-noise ratio. The signal conditioning unit 171 can include drive circuitry for operating the sensing modules 111 and 113 to perform the desired sensing mode for detecting the electrochemical signals and electrophysiological and/or physical signals from the user. The transceiver unit 173 can include an RF front-end unit, e.g., such as a Bluetooth Low Energy (BLE) chipset, that is capable of communicating with a microprocessor and manage the communication protocol of the wireless signal to be transmitted and/or received to another device, e.g., such as a user device (e.g., smartphone, tablet, smartwatch, smartglasses and the like) or the data processing system 120. The power supply 175 can include a battery, fuel cell or other power source to supply power to the components of the multimodal sensor 110.

In example embodiments that include transmission of the detected data by the multimodal sensor 110 to a user device, e.g., such as a smartphone, the system 100 can include a customized software application ("app") resident on the user device. The app includes program code that is stored in the memory of the user device and executable by a processor of the user device to perform various functions, e.g., including data processing, data display, and/or data storage. For example, the app can be implemented to process the detected signal data from the multimodal sensor 110. In some implementations, for example, the app can be implemented to control the transfer the of the detected signal data obtained by the multimodal sensor 110 to the data processing system 120.

In some embodiments, the data processing system 120 includes one or more computing devices in a computer system or communication network accessible via the Internet (referred to as "the cloud"), e.g., including servers and/or databases in the cloud. In some embodiments, the data processing system 120 can be embodied on a user device (e.g., a user's smartphone). In some embodiments of the system 100, for example, the data processing system 120 includes the one or more computing devices in the cloud and the app resident on the user device to receive and manage data processing of the data obtained by the multimodal sensor 110. In some implementations, for example, the multimodal sensor 110 transfers the detected signal data to the user device, e.g., using a low power wireless communication protocol (e.g., BLE), which the app on the user device can transfer to the one or more computing devices in the cloud of the data processing system 120 using a different communication protocol, e.g., including a wired or a wireless communication protocol such as LTE, Wi-Fi, or other.

In some embodiments, for example, the system 100 includes a remote user computer 130 to remotely monitor data associated with the user obtained by the multimodal sensor 110 and transferred to the data processing system 120, and/or to remotely operate aspects of the system 100. For example, the remote user computer 130 can include a personal computer such as a desktop or laptop computer, a mobile computing device such as a smartphone, tablet, smartwatch, etc., or another computing device.

In some example embodiments, the wearable multimodal sensor 110 on a single epidermal patch is referred to as a "Chem-Phys" patch. In some embodiments, a Chem-Phys patch device, for example, includes a screen-printed three-electrode amperometric lactate biosensor and two ECG electrodes, enabling concurrent real-time measurements of lactate and ECG. For example, when used in physical exertion monitoring, ECG measurements can help monitor heart health and function, while sweat lactate can be used to track an individual's performance and exertion level during physical activity. Sweat lactate is an important biomarker for tissue oxygenation and can act also as marker for pressure ischemia. By combining a lactate biosensor and an ECG sensor, the example Chem-Phys patch represents a powerful platform capable of simultaneously tracking both physico-chemical and electrophysiological changes of a human body, e.g., in real-time, thus providing a more comprehensive view of a person's health status than current wearable health or fitness monitors.

Figure 2:
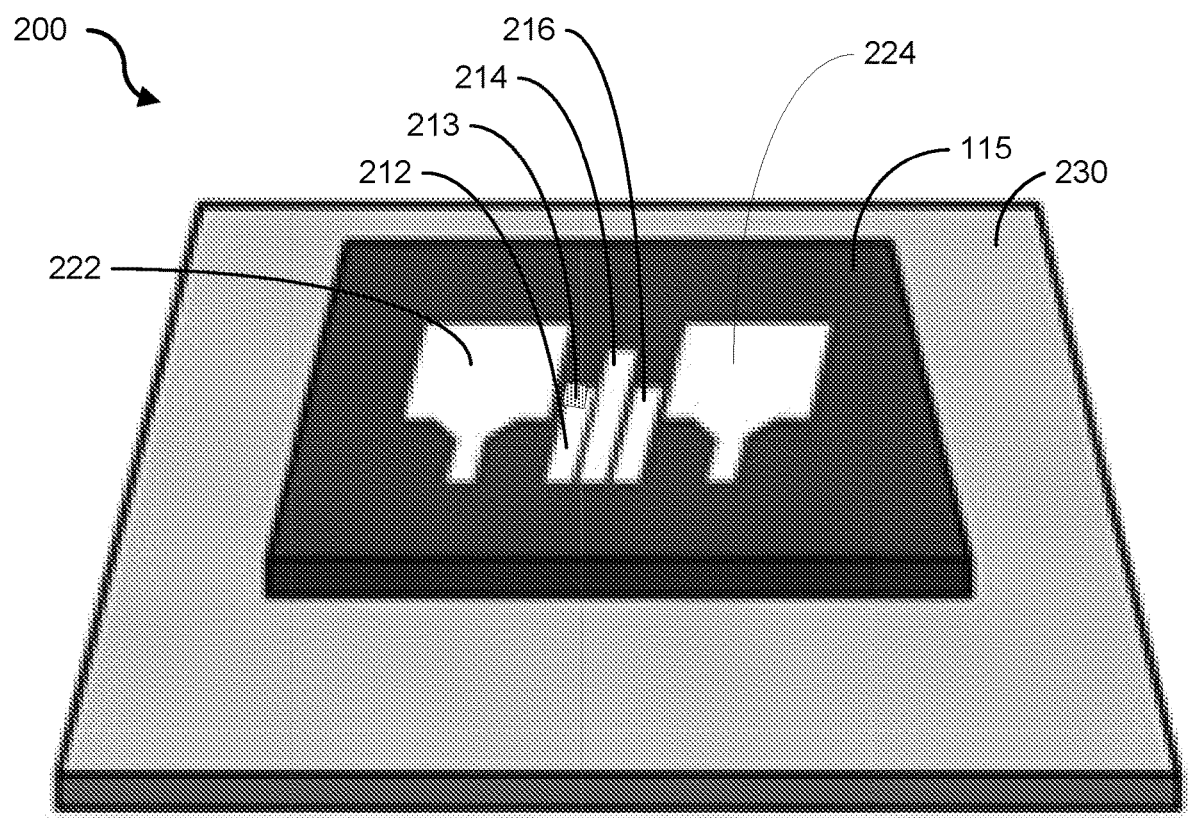
FIG. 2 shows an illustrative diagram of an example Chem-Phys patch that includes the electrochemical sensing module and the second sensing module on the flexible substrate.

FIG. 2 shows an illustrative diagram of an example Chem-Phys patch 200 that includes the electrochemical sensing module 111 and the second sensing module 113 on the flexible substrate 115. In some implementations, the Chem-Phys patch 200 can be stored on a temporary substrate 230, e.g., to hold the Chem-Phys patch prior to mounting on the skin of a user. The flexible substrate 115 of the Chem-Phys patch includes a thin, highly flexible polyester sheet that conforms well with the complex three dimensional morphology of the human skin, e.g., to provide a low-noise signal. The electrochemical sensing module 111 of the Chem-Phys patch 200 includes a working electrode 212 for an example lactate biosensor that is functionalized and coated with a biocompatible biocatalytic layer 213 (e.g., Lactate Oxidase-modified Prussian Blue). The electrochemical sensing module 111 of the Chem-Phys patch 200 includes a reference electrode 214 and a counter electrode 216, e.g., for amperometric measurements. In some implementations, the counter electrode 216 includes a functionalization coating, e.g., the biocompatible biocatalytic layer 213. The three amperometric electrodes of the Chem-Phys patch 200 are separated from one or more electrodes (e.g., electrodes 222, 224 in FIG. 2) of the second sensing module 113. In the example Chem-Phys patch 200 shown in FIG. 2, the electrodes 222, 224 include the Ag/AgCl ECG electrodes via a printed hydrophobic layer to maximize sensor stability and signal-to-noise ratio even in the presence of significant perspiration.

In the example embodiment, the Chem-Phys hybrid patch 200 has been designed to attain a compact form-factor with the three example lactate biosensor electrodes 212, 214, 216 in the center, and the two example ECG electrodes 222, 224 at each corner. The dimensions of the electrodes and the inter-electrode distances have been optimized (e.g., based on human trials) to acquire a clean ECG signal and lactate response with minimal interference between the two sensors.

The Chem-Phys patch 200 can include the electronics unit 117 included on the flexible substrate 115 or as an external device. In some implementations, for example, the two sensors (e.g., electrochemical sensing module 111 and the electrophysiological (ECG) sensor 113) can be interfaced to a custom printed circuit board (PCB) 317 featuring a potentiostat, an analog-to-digital converter (ADC), an analog front-end (AFE), and a Bluetooth Low-Energy (BLE) radio, e.g., for wireless telemetry of the results to a mobile platform, such as a smartphone or laptop. The Chem-Phys patch 200 can include interconnects (e.g., wires, conductive channels, etc.) between the electrodes of the electrochemical sensing module 111 and the electronics unit 117, and interconnects between the electrodes of the second sensing module 113 and the electronics unit 117.

Figure 3A:
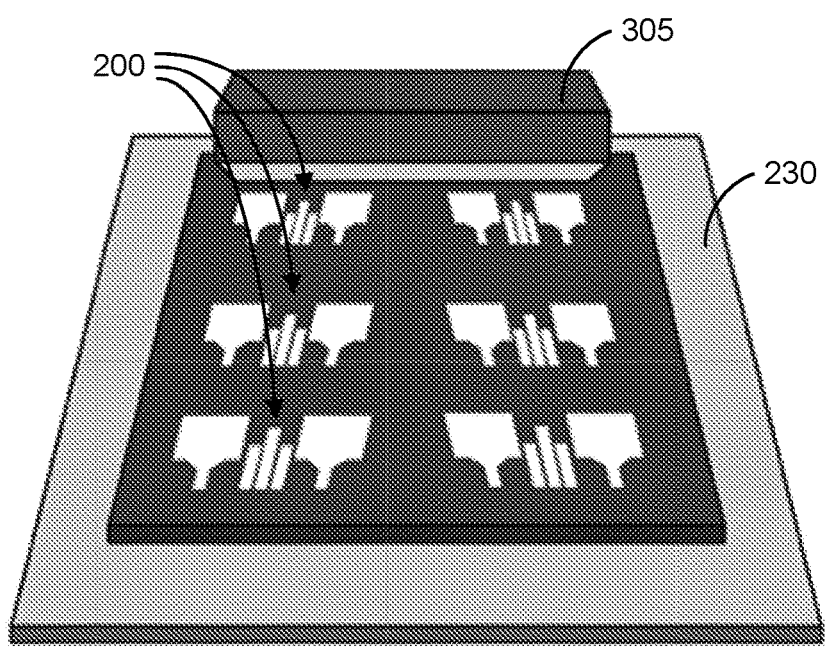
FIGS. 3A-3F shows diagrams and images associated with the example Chem-Phys patch monitoring device.
Figure 3C:
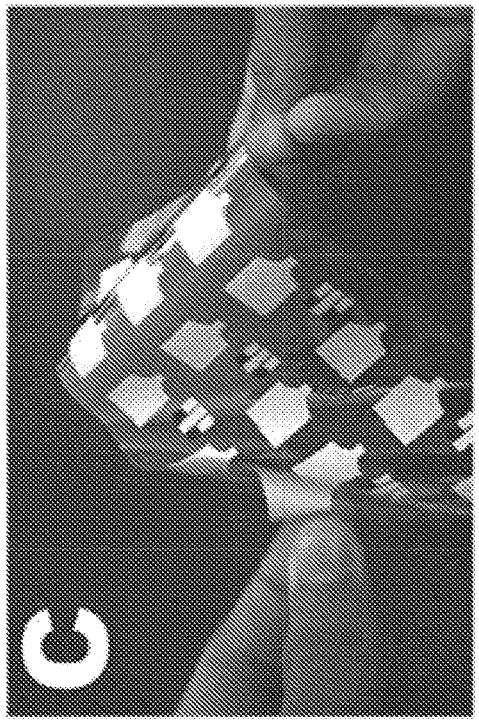
Figure 3B:
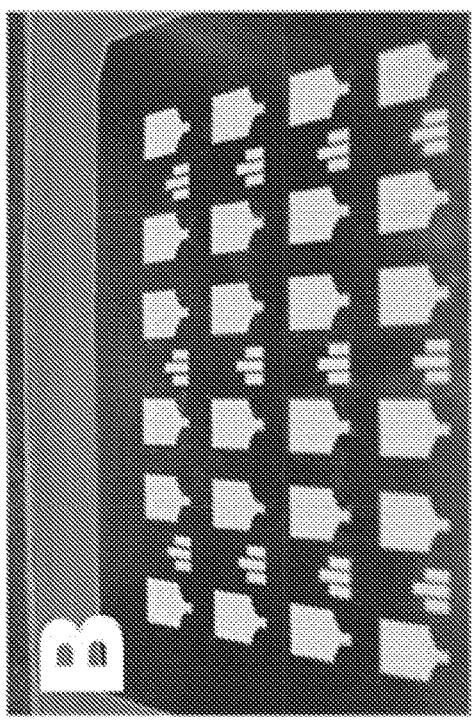
Figure 3D:
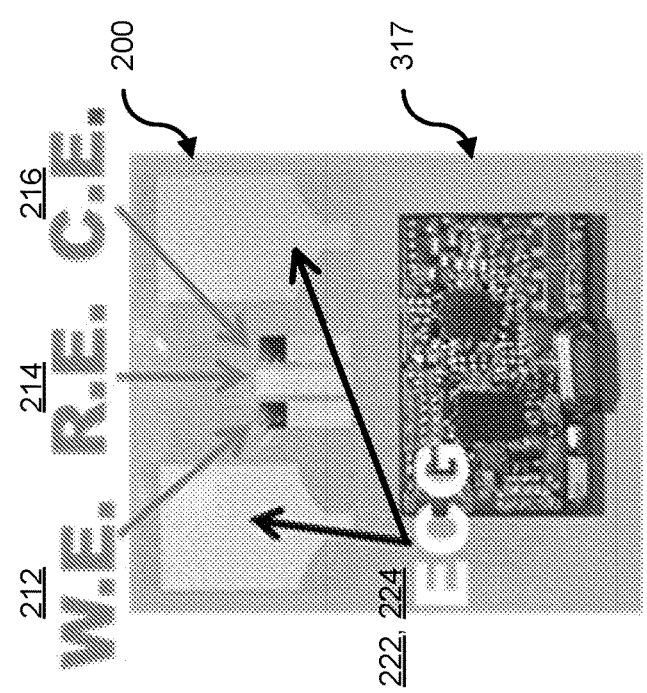
Figure 3E:
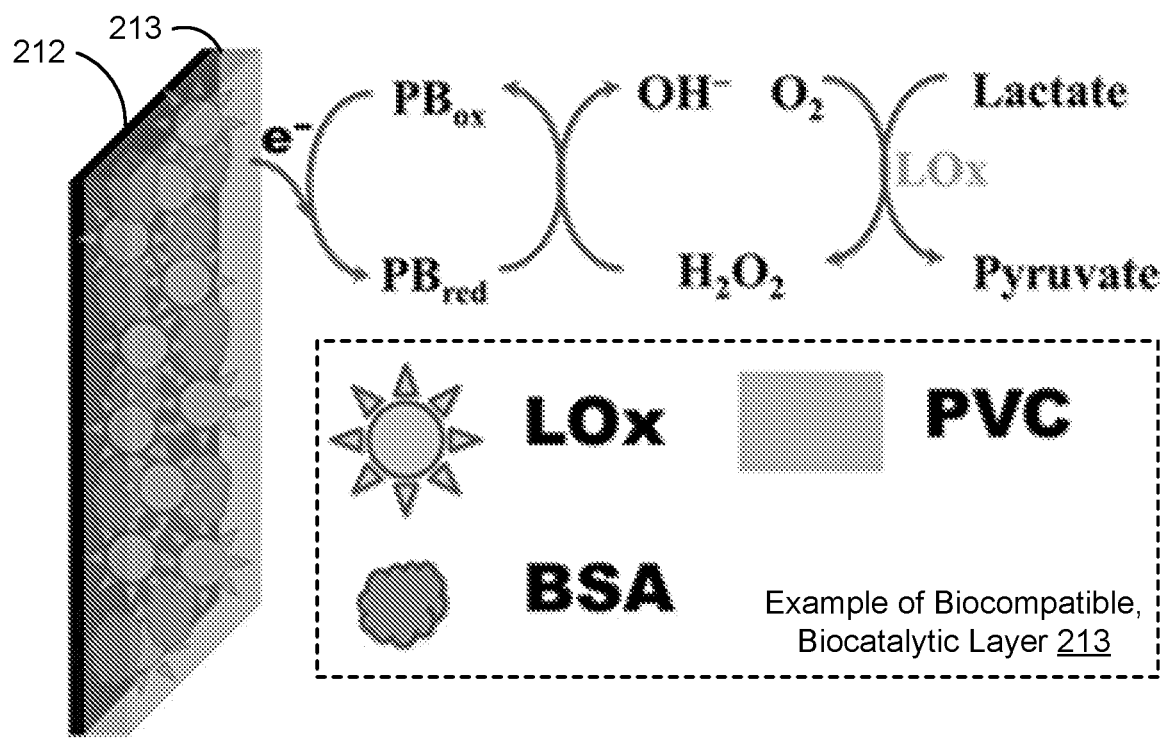
Figure 3F:
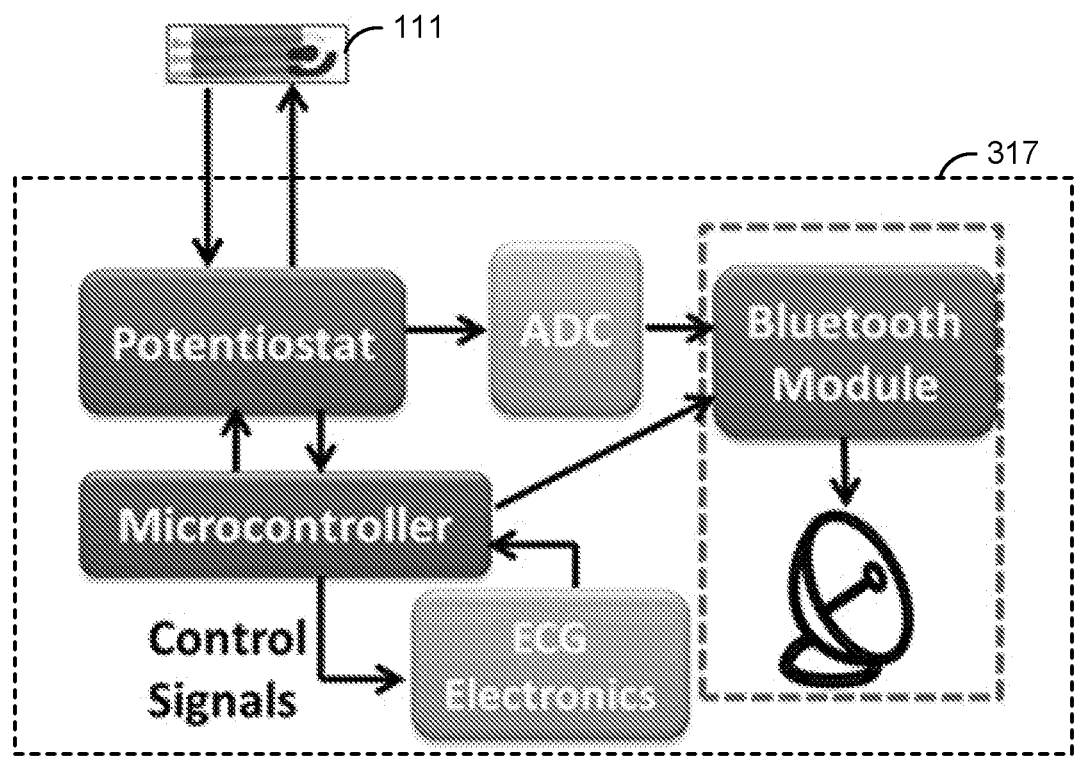

FIGS. 3A-3E shows diagrams and images associated with the example Chem-Phys patch 200 and electronics unit. FIG. 3A shows an illustrative diagram of an example screen printing process to produce an array of Chem-Phys devices on a flexible substrate. FIG. 3B shows an image of an example Chem-Phys printing stencil. FIG. 3C shows an image of an example flexible array of printed Chem-Phys patches 200. FIG. 3D shows an image of a fabricated example of the Chem-Phys patch 200 along with the example wireless electronics unit (e.g., customized PCB 317 featuring the potentiostat, ECG AFE, and BLE radio). The example Chem-Phys patch is wrapped around a glass rod (Ø=2 cm). FIG. 3E shows a cartoon diagram illustrating electrochemical sensing of lactate by the example LOx-based lactate biosensor module 111 of the Chem-Phys patch 200 along with the enzymatic and detection reactions. FIG. 3F shows a block diagram of the electronic circuit 117, e.g., which could be implemented to electrically interface with the electrochemical electrodes 212, 214, 216 and electrophysiological electrodes 222, 224.

Example implementations of the example Chem-Phys patch was used to monitor cardiac health related metrics, e.g., lactate measurements, and ECG and heart rate signals. The example results described herein show that lactate and ECG can be measured simultaneously, in which the lactate measurements do not adversely interfere with high-impedance ECG measurements, and that measurements of lactate levels and heart rate acquired from ECG data correlate with each other and with a commercially-available measurement device.

A hybrid multi-sensor system including the example Chem-Phys patch 200 and example PCB 317 was used to obtain real-time electrochemical and electrophysiological signals of human subjects. The example system was designed to be compact and easy to wear in a location that offers adequate access to both ECG signals and perspiration for lactate measurements. The system design was optimized to minimize sensor-body motion, minimize co-interference between the sensing modalities, and be of low-cost. These example requirements motivate a flexible epidermal electronic design that can be worn on the chest and fabricated using scalable fabrication techniques, e.g., using screen printing technology.

For example, the electrochemical biosensor electrodes of the Chem-Phys patch 200 were fabricated via low-cost screen printing technique using a screen printing device 305, conceptually illustrated in FIG. 3A, e.g., utilizing custom-designed stencils as shown in the photograph of FIG. 3B. The Chem-Phys patches were printed onto a highly flexible, thin polyester sheet (e.g., 50 µm thickness) for realizing highly conformable sensor patch that adheres well to the human skin without causing any discomfort. An array of fabricated sensors is shown in FIG. 3C. In some implementations, the total patch size can be dictated by the bipolar ECG electrodes, which are separated by a minimum distance in order to attain a high quality signal, e.g., in which the minimum distance is in a range of 1 to 6 cm.

For example, single-lead monitoring systems such as in the present design are used for basic heart monitoring, arrhythmias diagnosis, or studying the effect of exercise on the heart, and are placed in the vicinity of the conventional V1-V6 chest lead locations. Electrode size, separation, and placement parameters were determined through a series of experiments involving placement of Ag/AgCl-based ECG electrodes of various sizes (e.g., 1×1 cm$^2$, 1.5×1.5 cm$^2$, 1.5×1 cm$^2$ and 2×2 cm$^2$) and separation distances (e.g., 1 to 6 cm) on subjects with different chest sizes, and observing the resulting ECG waveforms. The example study revealed that a compact patch that provides favorable ECG signal could be realized by placing 1.5×1.5 cm$^2$ ECG electrodes across the V1 and V2 lead sites with an inter-electrode distance of 4 cm, thereby measuring from the vantage point of the septal surface of the heart as suitable for diagnostics of arrhythmias and the effects of exercise on the heart. This sets an upper-end size of the patch to be 7×2 cm$^2$. The chest region is not only convenient for measurement of ECG, but also has a high sweat rate during physical excursion, and can thus serve as an appropriate location to also measure lactate levels in human perspiration. Additionally, the epidermis and muscle tissues over these locations do not experience complex three dimensional strains and remain fairly stable even during intense physical activities, making measurements here especially convenient.

The example implementations showed that since the performance of amperometric lactate electrodes is not compromised by reducing their dimension, they were fabricated between the two ECG electrodes, as depicted in the image of FIG. 3D. Each of the three electrodes have an active area of 3×2.5 mm$^2$. For example, the working electrode of the Chem-Phys patch 200 used in the example study was printed using Prussian Blue ink, e.g., due to the high selectivity of Prussian Blue towards hydrogen peroxide, a byproduct of the enzymatic oxidation of lactate. FIG. 3E shows an illustration of the enzymatic oxidation of lactate at the functionalized working electrode. The reference electrode of the Chem-Phys patch 200 used in the example study was printed using Ag/AgCl. Since sweat can provide an alternate electrically-conductive pathway between the ECG electrodes and also between the ECG and amperometric electrodes, thus leading to potential distortion of the recorded ECG signal, a printed hydrophobic layer of Ecoflex® was used to separate the amperometric (electrochemical) electrodes from the ECG electrodes to obviate direct electrical contact between the ECG and amperometric electrodes via sweat, and thereby minimizing the cross-talk between the two sensors. The entire Chem-Phys patch is highly flexible and can be smoothly mated on curved surfaces. Such flexibility is important for achieving unobtrusive wearable devices that cause no hindrance or irritation to the wearer.

In the example implementations for the study, the Chem-Phys patch 200 was interfaced to the custom PCB 317 including a potentiostat and ADC for amperometric data acquisition, a AFE for ECG data acquisition, and a BLE chip for wireless transmission. An image of the example PCB 317 is shown in FIG. 3D. FIG. 3F shows a block diagram of the example PCB 317. The potentiostat is electrically connected to the electrodes of the electrochemical sensing module 111, e.g., via interconnects, to receive electrical signals obtained at the electrodes and to provide control signals to conduct the electrochemical detection technique, e.g., amperometry technique. The potentiostat is coupled to the ADC to convert analog signal to digital signal data. The potentiostat is coupled to a processing unit (e.g., microcontroller) to control operations of the potentiostat and receive data associated with the detected signals from the electrochemical sensing module 111 for processing, inter alia. The processing unit can include the microcontroller coupled to a memory unit to store and/or buffer the data. The AFE is coupled to the processing unit (e.g., microcontroller) to control operations of the AFE and receive data associated with the detected signals from the electrophysiological sensing module 113 for processing, inter alia. The processing unit and/or ADC are coupled to the RF front-end unit (e.g., BLE chipset) to regulate transmission of the data to an external device.

Example in vitro implementations of the Chem-Phys patch 200 were performed. For example, lactate concentration in human sweat depends on a person's metabolism and level of exertion, and typically ranges from 0 to 25 mM. A wide linear detection range coupled with a fast response time is thus essential for continuous epidermal monitoring of lactate. For example, the operating potential of –0.1V (vs to Ag/AgCl) was selected based on the onset potential for electro-oxidation of lactate by the fabricated biosensor, obtained during cyclic voltammetry studies. When the biosensor comes in contact with lactate, the immobilized LOx enzyme catalyzes the oxidation of lactate to generate pyruvate and $H_2O_2$. The Prussian Blue transducer, then selectively reduces the $H_2O_2$ to generate electrons to quantify the lactate concentration, as illustrated in FIG. 3E.

Figure 4A:
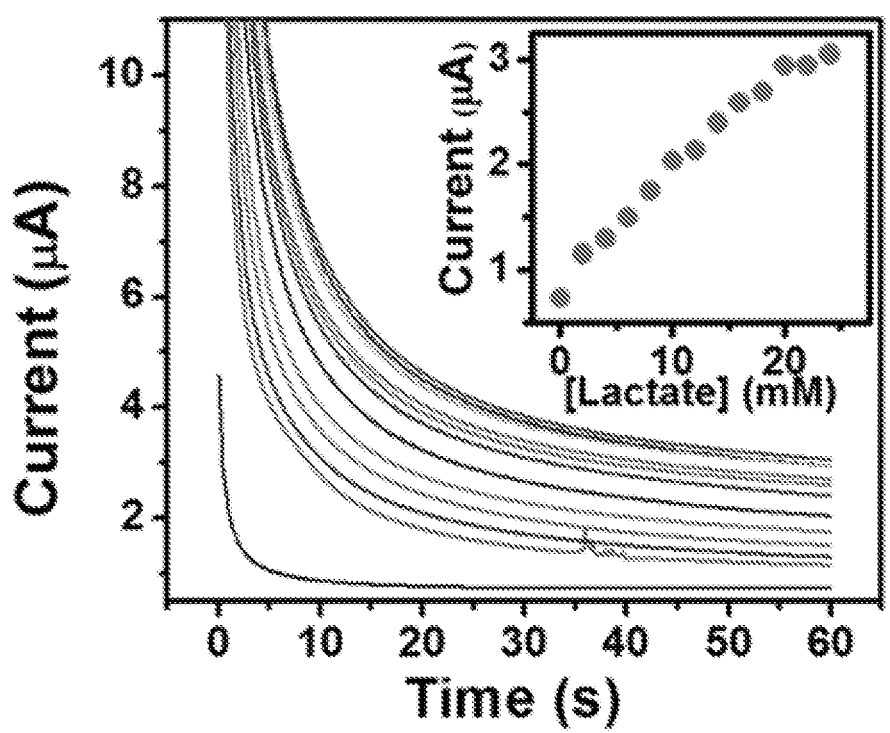
FIGS. 4A and 4B show data plots depicting an example in vitro characterization of the example Chem-Phys patch.

FIG. 4A shows a data plot of the amperometric response of an example lactate biosensor module of the Chem-Phys patch 200 to increasing lactate concentrations in the physiological range of 0-28 mM. It is evidenced from this plot that the biosensor responds linearly to the lactate concentrations in this range with a sensitivity of 96 nA/mM. Amperometric response to increasing lactate concentration from 0 to 28 mM with 2 mM additions in phosphate buffer (e.g., pH 7.0); applied voltage=–0.1V vs Ag/AgCl.

Figure 4B:
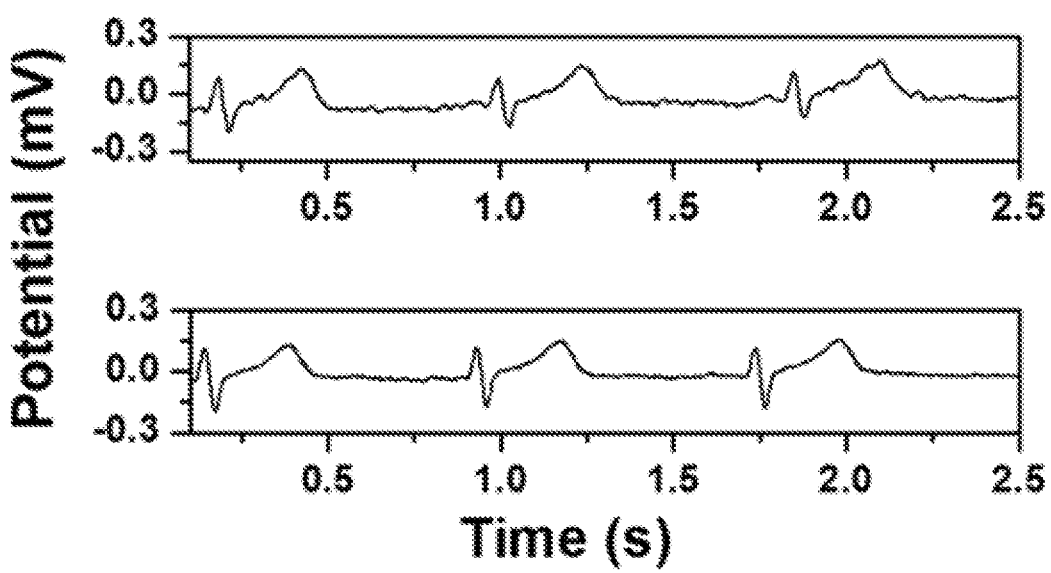

The ability of the printed ECG electrodes of the Chem-Phys patch 200 to record ECG signals was validated by comparing recordings from the fabricated electrodes to commercially-available 3M™ Red Dot™ ECG electrodes. FIG. 4B shows a data plot depicting ECG signals using 3M Red Dot electrodes (top), and an example printed ECG sensor of the Chem-Phys patch 200 (bottom). As illustrated in data plot, the ECG signals were recorded for the same subject using the commercial sensors and the example fabricated electrodes at the same location, and the detected ECG signals have similar morphologies when acquired using the same AFE circuitry.

Figure 5B:
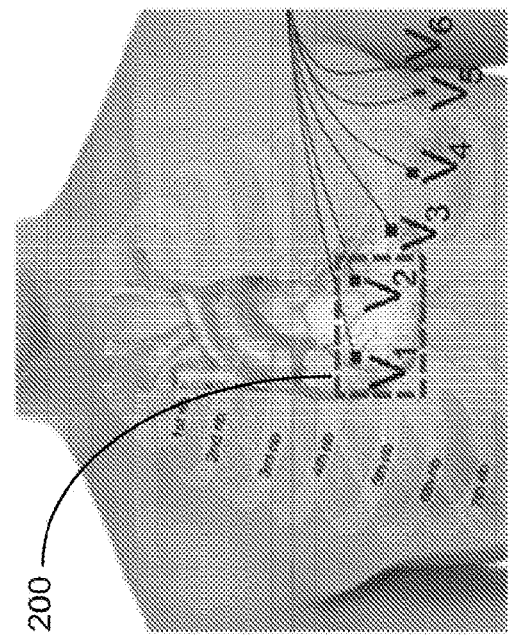
FIG. 5A-5D show images depicting the on-body configuration of the example Chem-Phys patch and data plots of example data from epidermal measurements using the Chem-Phys patch.
Figure 5A:
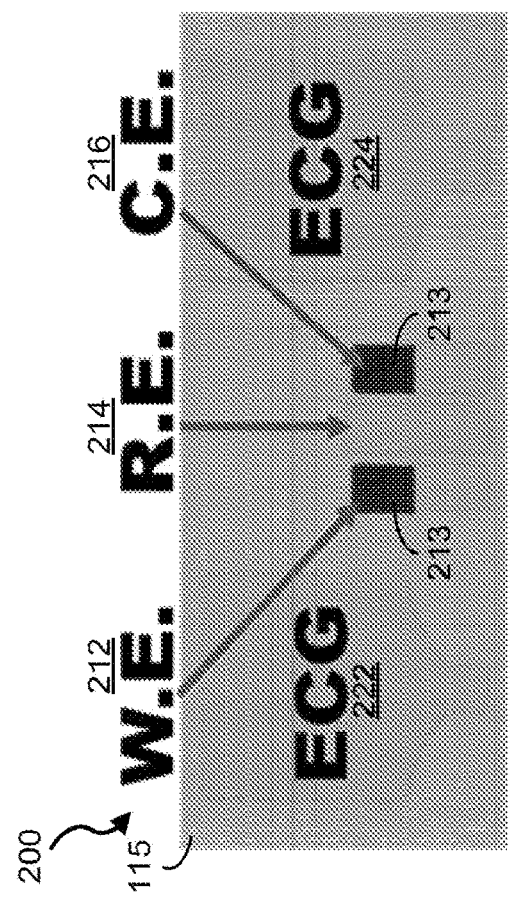

Example implementations of the Chem-Phys patch 200 for epidermal evaluations were performed. FIG. 5A-5D show images depicting the on-body configuration of the example Chem-Phys patch 200 and data plots of example data from epidermal measurements using the Chem-Phys patch 200. The example Chem-Phys patch 200 used in the study, shown in the photograph of FIG. 5A, was fabricated and applied to three healthy male subjects on the fourth intercostal space of the chest. FIG. 5B shows the location of the Chem-Phys patch 200 for mounting on the human body; fourth intercostal space of the chest. Dynamic changes in sweat lactate levels and ECG signals were measured continuously during a bout of intense cycling. In order to ensure that the anaerobic metabolism was invoked, subjects were asked to mount a stationary cycle and maintain a steady cycling cadence while the cycling resistance increased periodically, as illustrated in cycling resistance diagram for on-body tests of FIG. 5C.

Figure 5D:
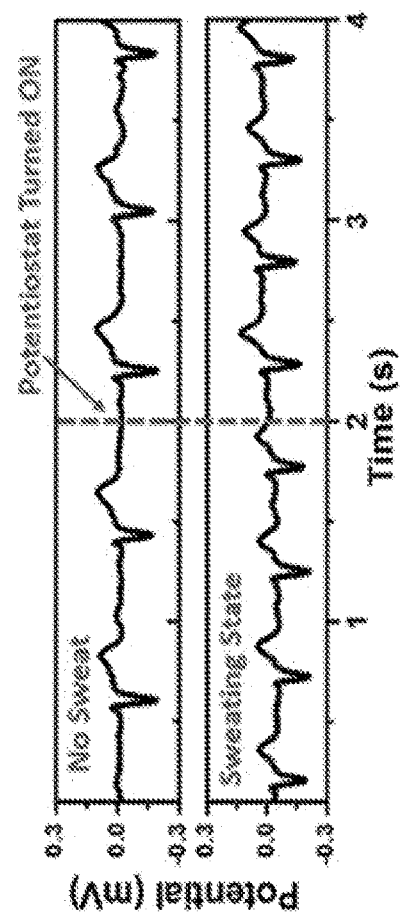
Figure 5C:
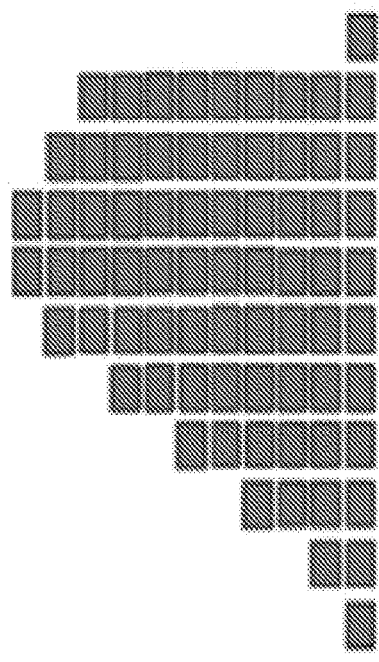

FIG. 5D shows a data plot depicting the effect of amperometric measurement on the ECG signal before cycling (e.g., no sweat state) and during cycling (e.g., sweating state). Since ECG measurements were made via bipolar high-impedance electrodes, and lactate measurements were made by applying a constant potential via a low-impedance potentiostat output and measuring current, for example, there was a possibility that a change in the applied potentiostat voltage (e.g., during start-up) could interfere with ECG measurements during the settling time of the potentiostat. At the same time, sweat included many ions and could thus act as an electrically conductive medium that can shunt the lactate and ECG sensors, or the two ECG electrodes together. The example Chem-Phys patch 200 is configured to simultaneously detect electrochemical signals and electrophysiological signals that overcome the aforementioned potential problems. For example, co-sensor interference and shunting effects were mitigated by geometrically separating the lactate and ECG electrodes and printing two vertically-oriented hydrophobic layers were next to the lactate biosensor, thereby facilitating flux of new perspiration across the biosensor itself, while minimizing shunting between the lactate and ECG sensors. For example, to validate performance of the example Chem-Phys patch 200 under concurrent hybrid sensing scenarios, the Chem-Phys sensor was mounted on a human subject and set to continuously record ECG prior to, during, and immediately after turning on the −0.1 V potentiostat output. The example results, obtained via a wireless Bluetooth link as shown in FIG. 5D, reveal that the potentiostat has a negligible effect on the morphology of the ECG signals, irrespective of whether the subject was in a resting or cycling state.

For example, to validate performance under realistic conditions, the example Chem-Phys patch 200 was tested on three subjects during 15-30 minutes of intense cycling activity; continuous time-series results during each experiment are shown in FIGS. 6A-6E. FIGS. 6A-6E show data plots of example real-time, on-body evaluations of the example Chem-Phys hybrid patch showing the lactate levels and heart rate for three human subjects. The plots represent real-time lactate concentration profiles for each subject (labeled "lactate") obtained by the electrochemical electrodes of the Chem-Phys patch, and heart rate data (labeled "H.R.") obtained by the ECG electrodes of the Chem-Phys patch. The plots include control heart rate data recorded by the Basis Peak® heart rate monitor (labeled "Basic Peak"). FIG. 6A shows example real-time ECG data obtained before the cycling bout for each subject in the three vertically-stacked data plots, and the real-time lactate concentration profiles and heart rate in beats per minute in the two vertically-stacked data plots. FIG. 6B shows example real-time ECG data obtained during the cycling bout for each subject, and the real-time lactate concentration profiles and heart rate in beats per minute in the two vertically-stacked data plots. FIG. 6C shows example real-time ECG data obtained after the cycling bout for each subject, and the real-time lactate concentration profiles and heart rate in beats per minute in the two vertically-stacked data plots. FIG. 6D shows a data plot providing more data for heart rate verifications. FIG. 6E shows a data plot demonstrating the response of the control amperometric sensor (e.g., without Lox enzyme) for subject #1.

At the commencement of the cycling activity, each subject's heart rate, extracted from ECG data, was within the normal resting range of 60 to 120 beat per minute (BPM). At the same time, a negligible current response was measured by the lactate biosensor module due to the lack of perspiration. With time, the resistance for cycling was increased (e.g., example shown in FIG. 5C), causing the subjects to exert increasing levels of effort to maintain constant cycling speed. This resulted in increasing heart rate and generation of sweat. At the onset of perspiration, lactate is released from the epidermis, and is selectively detected by the LOx-based biosensor module. As the resistance increases, the sweat lactate concentration too increases, showing a correlation between physical exertion, heart rate, and lactate generation. As the cycling continued, the sweat rate for each subject increased, leading to the well-documented phenomenon of dilution factor that causes decrease in the lactate concentration. The final stage of the cycling bout involved a 3 minute cool down period. During this phase, as expected, the heart rate normalized back near to the normal resting heart rate. At the same time, the lactate concentration measured by the lactate biosensor module continued to decrease.

The lactate biosensor data for each subject resembles the expected sweat lactate profile for increasing intensity workouts. For example, to validate that lactate, not other sweat constituents, was specifically measured, a control experiment in which an unmodified (Lox-free) amperometric biosensor was used under the same experimental conditions as above to subject #1. As shown in the data plots of FIG. 6E, the control biosensor leads to a negligible current response without the presence of LOx, confirming the high selectivity of the lactate biosensor. To validate ECG data over long time series, for example, even under the presence of experimentally-induced motion, heart rate as extracted from the ECG data is benchmarked against a commercial wristband heat rate monitor (BASIS®) for subjects 1 and 3. Extracted heart rate data matched the wrist-worn device with a Pearson correlation coefficient of r=0.975.

The example Chem-Phys sensor patch 200 fuses the monitoring of vital signs with on-body chemical sensing into single fully printable wearable platform. On-body epidermal implementations using the example Chem-Phys patch 200 in a realistic fitness environment revealed that ECG sensing is in-line with existing wearable devices, and is not adversely affected by the simultaneous measurement of lactate via constant-potential amperometry. For example, the lactate control study using an enzyme-free amperometric sensor and correlation of the heart rate data of the hybrid patch to that recorded by a commercial heart rate monitor underscore the promise of the Chem-Phys patch 200 to monitor simultaneously ECG signals and sweat lactate levels for tracking the wearer's physicochemical and electrophysiological status. This device represents an example of multimodal wearable sensors in accordance with the present technology that fuse chemical, electrophysiological, and physical sensors for more comprehensive monitoring of human physiology.

The following describes example fabrication methods to produce the multimodal sensor 110, e.g., such as the Chem-Phys patch 200.

Example reagents, cells and solutions used in the example implementations included the following. Chitosan, acetic acid, polyvinyl chloride (PVC), tetrahydrofuran (THF), bovine serum albumin (BSA), L-lactic acid, sodium phosphate monobasic, and sodium phosphate dibasic were obtained from Sigma-Aldrich (St. Louis, Mo.). L-Lactate oxidase (LOx) (activity, 101 U/mg) was procured from Toyobo Corp. (Osaka, Japan). Reagents were used without further purification. Prussian blue conductive carbon (C2070424P2), Ag/AgCl (E2414) and insulator (Dupont 5036) inks were procured from Gwent Group (Pontypool, UK), Ercon Inc. (Wareham, Mass.) and Dupont (Wilmington, Del.). ECG hydrogel conductive adhesive (RG63B, 35-mil thick) was obtained from Covidien. Polyester sheets (MELINEX® 453, 50 μm thick) were provided by Tekra Inc. (New Berlin, Wis.).

Example instrumentation used in the implementations included the following. The example Chem-Phys patch 200 was printed by employing an MPM-SPM semiautomatic screen printer (Speedline Technologies, Franklin, Mass.). Sensor patterns were designed in AutoCAD (Autodesk, San Rafael, Calif.) and fabricated on stainless steel through-hole 12 in.×12 in. framed stencils (Metal Etch Services, San Marcos, Calif.). Electrochemical characterization was performed at room temperature using a CH Instruments electrochemical analyzer (model 630C, Austin, Tex.). A CONTEC MS400 Multi-parameter Patient Simulator, ECG simulator has been utilized for testing of ECG instrumentation circuits. 3M Red Dot Multi-Purpose Monitoring electrodes are used for verification of collected signal using the fabricated ECG sensors.

The Chem-Phys hybrid patch was fabricated via screen printing technology while the wearable electronic board was realized by relying on standard 4-layer PCB fabrication and assembly protocols. For example, the Chem-Phys patch was fabricated in-house by printing a sequence of Ag/AgCl, Prussian Blue and insulator inks were patterned on the highly flexible transparent polyester substrate by employing the custom designed stencils and screen printer. The Ag/AgCl and insulator ink was cured at 90° C. for 10 min, while the Prussian Blue ink was cured at 80° C. for 10 min in a convection oven.

Upon printing of the hybrid patch, the working electrode of the amperometric sensor was functionalized with LOx enzyme. The LOx solution (40 mg/mL containing 10 mg/mL BSA stabilizer) was mixed with a chitosan solution (0.5 wt % in 1 M acetic acid) in a 1:1 v/v ratio. Subsequently, 8 µL droplet of the above solution was casted on the electrode and dried under ambient conditions. Thereafter, 4 µL of PVC solution (3 wt % in THF) was drop casted and allowed to dry under ambient conditions for at least 3 h before use. The ECG electrodes were covered with conductive hydrogel adhesive. The patch was then affixed to a medical grade adhesive sheet required for applying to human skin. The patch was stored at 4° C. when not in use.

The example PCB 317 used in the example implementations was produced by the following techniques. A 4-layer Bluetooth-enabled PCB employed a Texas Instrument (TI) CC2541 BLE System-on-Chip for communication and processing. An ADS1293 analog front end chip was employed for biopotential measurements to record the electrocardiogram (ECG) signals from the fabricated ECG electrodes. An LMP91000 analog front end, programmable through an I2C interface driven by the CC2541, was used as the on-board potentiostat for lactate concentration determination. The data from each sensor was collected by the CC2541 and transmitted to a Bluetooth 4.0-enabled receiver. A graphical interface was developed using Python to demonstrate measurement results on a PC. A Johanson Technology 2.45 GHz chip antenna (2450AT42A100) and impedance-matched balun (2450BM15A0002) were employed for wireless transmission. A CR2032 button cell lithium battery (3 V, 220 mAh) was utilized as a power source, regulated for the electronics via a TPS61220 boost converter. In the "active mode", the board consumed, on average, 5 mA from a 3 V supply (15 mW).

Characterization of the amperometric lactate sensor module in the example implementations included the following. These studies were performed using a 0.1 M phosphate buffer (e.g., pH 7.0) solution. The operating potential for the lactate sensor was selected by using cyclic voltammetry. The amperometric response was recorded after 1 min incubation in the sample solution, using a potential step to −0.1 V (vs Ag/AgCl) for 60 s.

Characterization of the ECG sensor module in the example implementations included the following. ECG monitoring has been performed using both commercial 3M Red Dot Multi-Purpose monitoring electrodes, as well as fabricated ECG electrodes to verify the functionality of the printed Ag/AgCl ECG sensors.

The on-body epidermal evaluation of the example Chem-Phys patch was performed in strict compliance with the protocol that was approved by the institutional review board (IRB) at the University of California, San Diego. The study was deemed by the IRB as posing "no greater than minimal risk" to the prescreened subjects who were recruited for the investigation. A total of 3 healthy male volunteers (recruited in response to follow-up from flyers) with no prior medical history of heart conditions, diabetes, or chronic skeletomuscular pain were recruited for participation in the study, and informed, signed consent was obtained from each individual following a rigorous prescreening procedure. A typical study comprised of applying the Chem-Phys hybrid patch on fourth intercostal space of a subject's chest in order to record the ECG signal between V1 and V2 positions.

Subjects were then asked to mount a stationary cycle and begin cycling at a steady, comfortable cadence. Subjects were instructed to maintain their cadence while an increasing resistance was applied at 3 min intervals. The absolute resistance level and duration was selected according to subject's fitness level while the same intensity profile was used throughout the human studies. This ensured that the anaerobic metabolism was invoked at similar time scales, hence augmenting the excretion of lactate in the perspiration in a controlled fashion. Following the intense fitness bout, the volunteers were asked to gradually reduce their cadence during a 3 min "cool-down" period whereby the resistance was reduced from maximal levels.

The printed circuit board was assembled and tested to validate the functionality and performance. The potentiostat circuit was verified together with the lactate biosensor through an in-vitro amperometric experiment. The ECG AFE was characterized using a CONTEC MS400 Multiparameter Patient Simulator (ECG simulator). The output signal of the ECG simulator was read using ADS1293 analog front end chip, and transferred through BLE link to a BLE-enabled device.

In some embodiments of the multimodal sensor 110, a multimodal, real-time wearable health monitor device measures multiple physiological parameters including electrochemical parameters, electrophysiological parameters, and physical parameters simultaneously on a single platform. The device includes sensing techniques include amperometry for metabolite monitoring (e.g., glucose, lactate); potentiometry for electrolyte monitoring (e.g., K+, Na+, Cl—, pH); low-noise amplification for biopotential monitoring (e.g., ECG, EEG, EMG); and strain and temperature-induced resistivity changes for physical parameter monitoring (e.g., skin temperature via temperature-induced resistivity changes, respiration rate, strain, acceleration, etc.). For example, the device can be fabricated either within an epidermal temporary tattoo, a textiles patch, a band aid, or other flexible substrates. In some embodiments, electrolytes and metabolites are monitored in the wearer's perspiration. In some embodiments, electrolytes and metabolites are monitored in sub-dermal fluid using a reverse iontophoresis process.

In some example embodiments, the wearable multimodal sensor 110 on a single epidermal patch is referred to as a "FlexEM$^2$" device (Flexible Epidermal Multimodal health Monitoring). In some embodiments, a FlexEM$^2$ device, for example, includes one or more electrochemical sensing modules 111, an electrophysiological sensing module 113 and physical parameter sensing module 113 for simultaneous, real-time measurements of key metabolites (e.g., lactate, subdermal glucose, electrolytes, etc.), biopotentials (e.g., ECG) and physical parameters (e.g., respiration rate, skin temperature, etc.), respectively.

The FlexEM$^2$ device integrates electrochemical, electrophysiological and physical biosensors on a flexible, epidermal-mounted temporary tattoo-like patch that interfaces directly with ultra-miniaturized wireless electronics. As such, patients can leverage such devices in ambulatory, outpatient environments with minimal discomfort or obtrusiveness. As a low-cost printed platform that also leverages scaled semiconductor manufacturing, the developed FlexEM$^2$ device can be employed for widespread use as a general diagnostic tool, for preventive healthcare, or for monitoring of patients with chronic health issues, e.g., including cancer, congestive heart failure, diabetes, renal failure and obesity. For example, frail elderly patients could be monitored in real-time for early detection of conditions such as dehydration, electrolyte disturbances, hypoglycemia, and cardiac arrhythmias, any of which may precipitate a fall and subsequent injury.

For example, heart disease is the leading cause of death amongst in America, annually killing 600,000 people and costing the economy $108.9 billion dollars. A large fraction of this cost is attributed to re-admissions, e.g., approximately 50% of heart disease patients are re-hospitalized within 6 months, costing Medicare $17.4 billion annually. In theory, outpatient monitoring should enable patients to keep better track of their fitness, dietary, and pharmacological regimens in order to avoid re-hospitalization. However, in practice, commercially-available outpatient monitors are large, rigid, and inconvenient to wear, limiting patient acceptance and use, while also only monitoring a small number of parameters (such as electrocardiograms or ECGs, acceleration, and respiratory rate) that may not actually aid in changing patient behavior.

The multimodal sensor 110 (e.g., FlexEM$^2$ device) provides a wearable device that integrates flexible, anatomically-compliant materials with a multi-modal array of biosensors to increase use and utility of outpatient monitors. It is envisioned that use of the multimodal sensor technology can decrease re-hospitalizations of heart disease patients, while also providing other advantages or addressing other problems or diseases. For example, while ECG monitoring is well understood and clinically important, it is difficult to use this data to directly determine if therapy, exercise, or diet is actively decreasing heart disease risks, especially over short time periods. Interestingly, there are several other parameters one could potentially measure that can give a more rapid and direct indication to the patient on the current status of their health; for example, one of the most effective ways to reduce the burden of cardiovascular disease is to decrease the amount of salt intake. Thus, unlike current health monitoring products that typically only monitor ECG and a small handful of other physical parameters that may not have direct impact to heart disease patients, the multimodal sensor 110 can simultaneously monitor electrophysiology (e.g., ECG) and real-time non-invasive sub-dermal electrolytes (e.g., potassium, sodium, and pH) in a single platform. For example, by augmenting critical ECG recordings, used for algorithmically-driven emergency alerting, with electrolyte data, the multimodal sensor 110 can create a much faster feedback loop to keep patients proactive in their daily health regimens, while offering tremendous data fusion opportunities for medical research. Also, for example, the multimodal sensor 110 can empower clinicians to remotely monitor a patient's physiologic function, follow trends after medical intervention, and/or time interventions to prevent potentially harmful events from occurring, as well as empower the patients themselves to self-monitor to meet various goals, e.g., such as reducing salt-intake to safe/ useful levels and ensuring adequate exercise. The diagnostic, monitoring, and medical research opportunities enabled by the present technology thus have meaningful societal and commercial significance.

In some embodiments of the FlexEM$^2$ device, the device provides fully-equipped wireless multimodal sensors with ultra-low-power operation and designed for anatomically-miniaturized volume constraints. For example, such embodiments of the FlexEM$^2$ device includes electronic circuits that feature ultra-low-power biopotential and potentiometric instrumentation. In some embodiments, the FlexEM$^2$ device includes current drivers for reverse-iontophoresis-enabled sub-dermal sensing. For example, a Bluetooth Low Energy chipset with built-in microcontroller is employed in some embodiments of the FlexEM$^2$ device to relay sensed information to a smartphone or smartwatch platform. The FlexEM2 is designed to be a single low-cost, unobtrusive, robust and wearable platform.

For example, for patient usability of wearable sensors, the devices must be comfortable, unobtrusive, and have a long operational lifetime. The latter point is especially important as the number of sensor devices worn on the body grows, and patients will not tolerate recharging regimens for more than a small handful of devices.

The FlexEM$^2$ device is designed to meet requirements such as durability, light-weight, miniaturized and having intimate skin conformance. Moreover, the FlexEM$^2$ device provides a platform that can facilitate a plethora of multiple electrochemical, electrophysiological, and physical sensor modules for assessing vital signs, e.g., such as heart rate, respiration rate, oxygenation of the blood, skin temperature, bodily motion, brain activity, and blood pressure.

Figure 7:
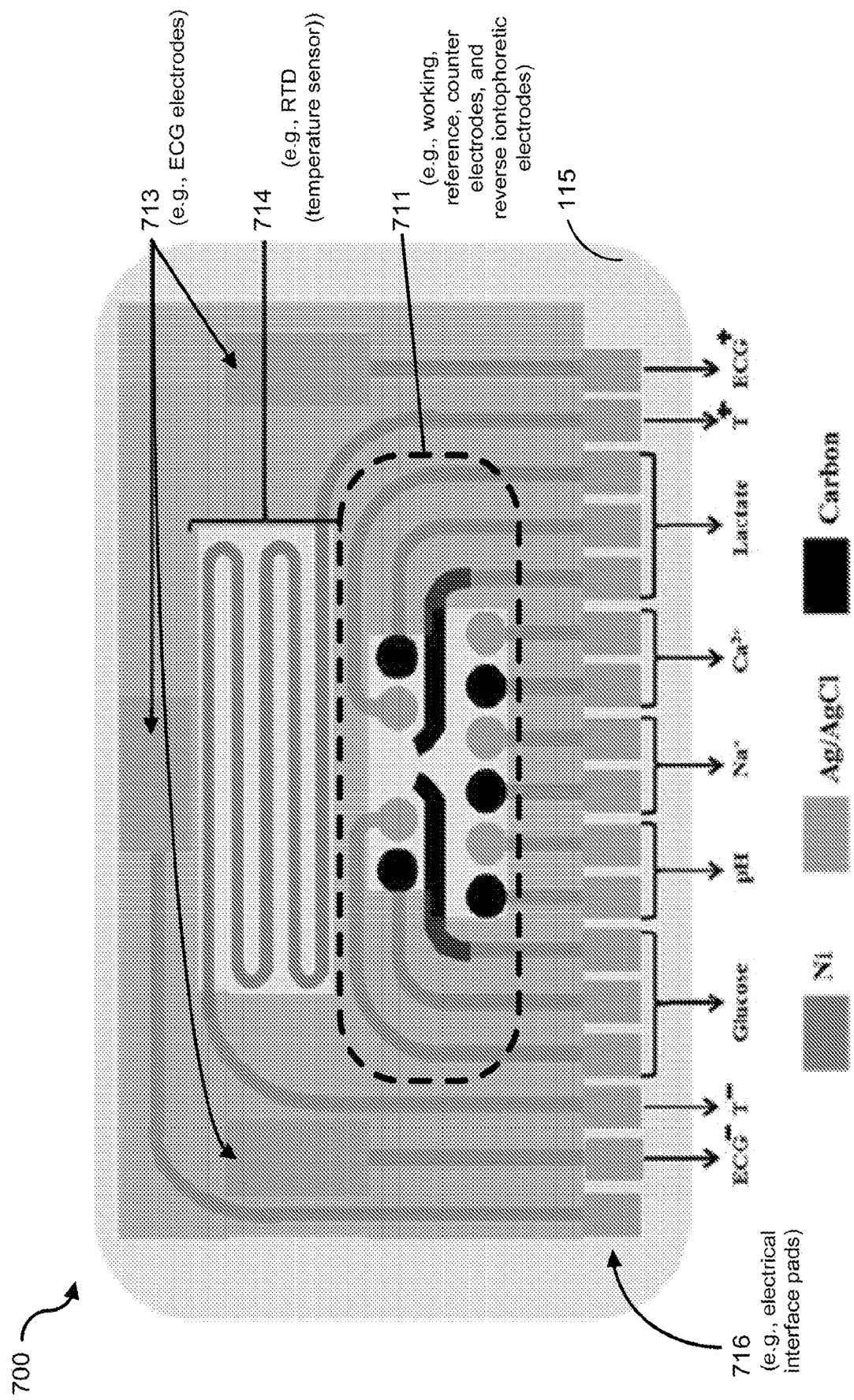
FIG. 7 shows a diagram of an example multimodal sensor device in accordance with some embodiments of the present technology.

FIG. 7 shows a diagram of an example embodiment of a FlexEM$^2$ device 700. The device 700 includes a multi-electrode electrochemical sensing module 711 and the second sensing module 113, including an electrophysiological sensing module 713 and a physical parameter sensing module 714, on the flexible substrate 115. In some embodiments, the flexible substrate 115 includes a thin, highly flexible material that conforms well with the complex three dimensional morphology of the human skin. In some embodiments of the device 700, the electrochemical sensing module 711 includes one or more working electrodes coated with a biocompatible biocatalytic layer specific to a target analyte. For example, a lactate biosensor module can include a working electrode coated with Lactate Oxidase-modified Prussian Blue, and a sub-dermal glucose biosensor module can include a working electrode coated with Glucose Oxidase-modified Prussian Blue. The electrochemical sensing module 711 of the device 700 includes corresponding reference electrode(s) and/or counter electrode(s) to the respective working electrode(s), e.g., for various electrochemical sensing techniques including but not limited to amperometric measurements. In some implementations, the counter electrode(s) of the electrochemical sensing module 711 includes the functionalization coating, e.g., such as that of the working electrode. The electrodes of the electrochemical sensing module 711 are separated from electrodes of the electrophysiological sensing module 713 and a physical parameter sensing module 714. In the example device 700 shown in FIG. 7, a coil-like electrode structure is configured to form a resistance temperature detector and is positioned on the flexible substrate 115 above the region where the electrodes of the electrochemical sensing module 711 are positioned. Also shown in FIG. 7, the device 700 includes electrodes of the electrophysiological sensing module 713 positioned at least partially around the electrode(s) of the physical parameter sensing module 714 and the electrochemical sensing module 711. In some embodiments, the electrodes of the electrophysiological sensing module 713 and the physical parameter sensing module 714 include nickel (Ni). The device 700 includes an electronics unit 717 that electrically interfaces with the electrochemical sensing module 711, the electrophysiological sensing module 713 and the physical parameter sensing module 714 via electrical contacts 716. In some embodiments, some or all of the components of the electronics unit 717 are fabricated on the flexible substrate 115; whereas in some embodiments, the electronics unit 717 is independent of the flexible substrate 115 and electrically connected through interconnecting wires.

In some implementations, device 700 can be fabricated on a temporary transfer tattoo-based flexible substrate that intimately conforms to the patient's skin for simultaneous detection of the non-invasive chemical and physiological analysis directly on the epidermal surface. Confining the sensor array onto the contours of the epidermis includes layout, size and spacing design factors including integration of potentiometric and amperometric electrolyte/metabolite sensing components capable of achieving robust electrochemical performance, as well as structural resiliency to withstand repeated mechanical stress for continuous epidermal wear. The device 700 can be fabricated using screen printing with printed inks modified for reinforcing the electrode transducers.

The device 700 can be produced based on integration of thick-film (e.g., screen-printing) processes with flexible plastic substrates, capable to adhere and conform to the epidermis, for fabricating an array of electrochemical sensors, ECG sensors, and a temperature/strain sensor. In some embodiments, the printable electrode arrays for the electrochemical sensing module 711 include three sets of epidermal solid-contact ion-selective electrodes (ISE) for potentiometric measurements of sweat electrolytes (e.g., sodium, calcium and/or pH) and two sets of enzyme-based biosensor electrodes for selective amperometric monitoring of lactate and glucose, e.g., each including a working electrode, reference electrode and counter electrode. The five example electrode sets of the electrochemical sensing module 711 are integrated with two sets of physical sensors and a set of electrophysiological electrodes, which can be printed using the corresponding transducer materials onto a suitable plastic support (e.g., Mylar, PET, and PTFE (Teflon)). The example device 700 shown in FIG. 7 displays a design of the pattern of the printed sensor array including the corresponding electrical contacts 716. In some embodiments of the device 700, the electrochemical sensing module 711 includes a reverse iontophoretic electrode structured on the flexible substrate 115 to at least partially encompass the working electrode and the counter/reference electrodes for the respective electrochemical biosensor. The reverse iontophoretic electrodes can be operated to apply an electric field to drive ion flow from interstitial fluid (ISF) toward the working electrode and the counter/reference electrode.

For example, the absence of reliable wearable and conformal chemical sensors has greatly hindered progress in the area of wearable devices for health monitoring. Real-time, non-invasive analysis of key electrolytes in sweat and sub-dermal metabolites would provide continuous physiologically-relevant chemical data that are not available from existing technologies, offering very useful insights into the health status of the individual. For example, conventional sensors that obtain chemical information from human subjects are typically performed in clinical labs or Point-of-Care (PoC) devices, where such approaches do not support continuous, real-time measurements, limiting their utility to applications where stationary, infrequent tests are sufficient. While recent work has demonstrated that chemicals such as electrolytes and metabolites can be measured continuously using epidermal electronics on the skin, or through non-invasive monitoring of other bodily fluids, these devices measure only a single parameter at once, and are not integrated with other sensing modalities.

Moreover, chemical information has been commonly obtained via infrequent fingerstick blood draws. However, such fingerstick analysis of metabolites and electrolytes implies a level of invasiveness and pain that has not traditionally been compatible with the wearer's daily life. In addition, such measurement paradigms have naturally slow sampling rates: only one measurement point can be acquired per blood draw. The device 700 shown in FIG. 7 is capable of real-time chemical sensing through integration of reverse iontophoresis and potentiometric/amperometric electronics onto a single, wearable patch, with information delivered wirelessly to a smartphone-type device.

The pattern of the device 700 is designed based on various considerations such as reducing potential cross talk among neighboring electrodes, signal-to-noise characteristics, and the realization of convenient electrical contacts. As illustrated in FIG. 7, the resulting printed array includes two metabolite enzymatic biosensors for glucose and lactate, three electrolyte potentiometric sensors for sodium, calcium and pH, a temperature transducer, and three ECG electrodes, all accommodated on a small plastic substrate (e.g., ~1×1 in$^2$). The fabrication of this example device 700 includes printing of corresponding Ag/AgCl reference electrodes and counter electrodes, and nickel material for the ECG electrodes and temperature transducer. A microchannel gap, included around the electrode area (e.g., using proper thin spacers), can facilitate the flux of fresh perspiration over the sensor array. An ultra-low-power dual-purposes skin strain and temperature sensor can be configured by monitoring the impedance of two resistance temperature detector (RTD) traces printed on the epidermal patch. By employing two separate traces made of nickel and chromium, respectively, for example, the device 700 can compensate temperature measurements for strain, while simultaneously sensing the strain itself (e.g., for respiration monitoring).

Fabrication techniques to produce the device 700 includes consideration of various factors associated with the underlying transducers, e.g., the ink composition/modification and printing/curing conditions. The printed inks can be modified for reinforcing the electrode transducers and imparting structural resiliency. Deposition and entrapment of the enzyme- or ionophore-based reagent layers for the metabolites and electrolyte detection, respectively, can be achieved to selectively attach the reagents to the electrodes to facilitate the electrochemical reactions with the target analyte. For example, additives such as enzyme stabilizers, plasticizers or cross linkers can be used, e.g., with proper toxicity and leaching considerations, along with coverage with a biocompatible layer.

The outer layers prevent direct contact with the skin and leakage of components of the reagent layer. These layers will also provide high-degree of permelectivity by ensuring facile diffusion of lactate or glucose while rejecting co-existing electroactive and fouling constituents. A variety of biocompatible layers can be used for the electrochemical detection techniques, e.g., including electropolymerized polypyrrole, chitosan or Nafion.

Figure 8:
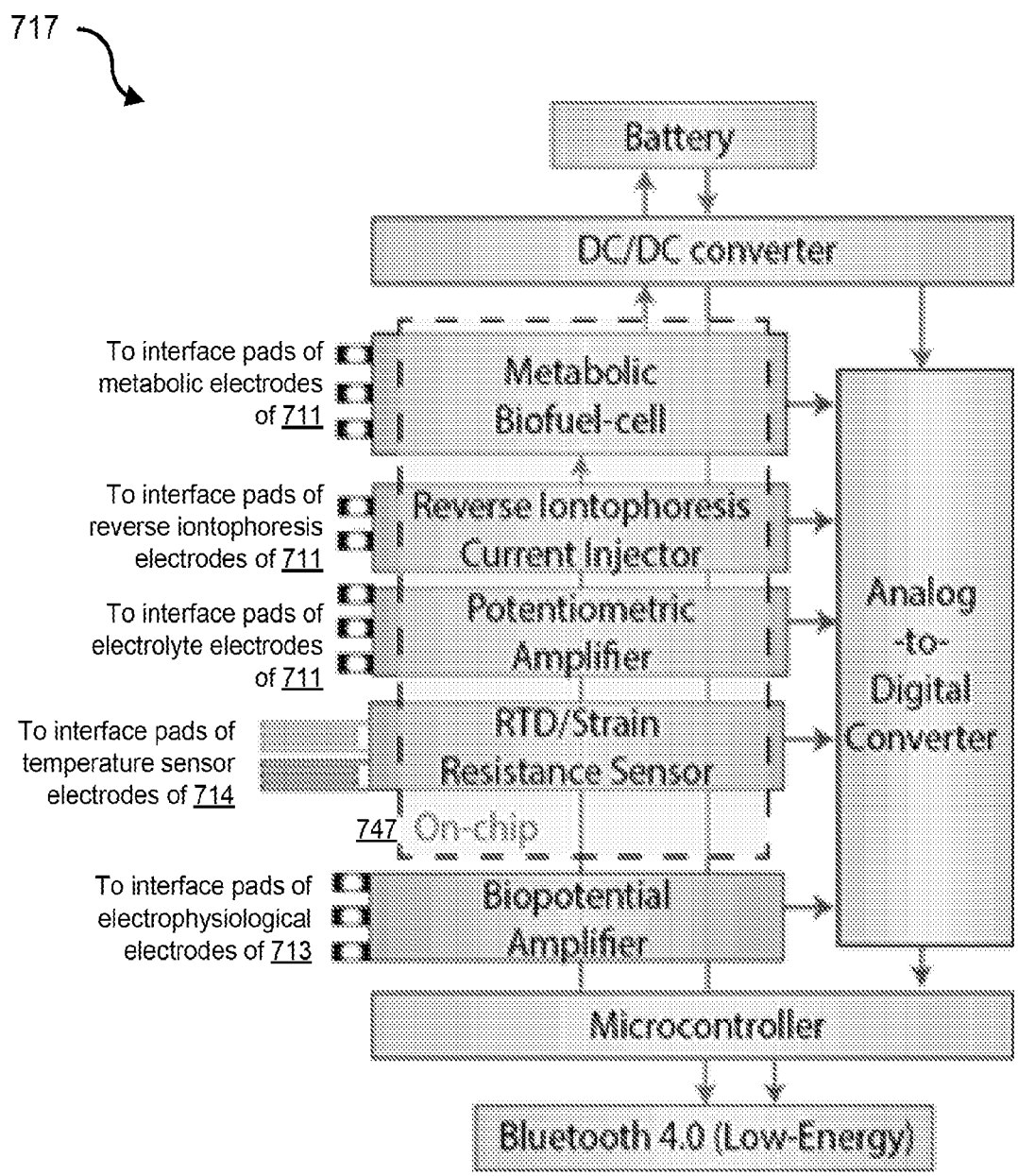
FIG. 8 shows a block diagram of an example electronics unit to electrically interface with the sensors of the example device of FIG. 7.

FIG. 8 shows a block diagram of an example electronics unit 717 to electrically interface with the sensors of the device 700. The electronics unit 717 includes amplifiers and/or drivers for metabolic electrodes, current injectors for reverse iontophoresis, potentiometric amplifier, and an amplifier to condition skin temperature signals, which meet size constraints (e.g., of or less than 2 mm$^2$) and total power consumption specifications (e.g., of or less than 100 μW) for the described example wearable monitoring applications. The electronics unit 717 can include a customized integrated circuit (IC) 747, e.g., on a single microchip, that includes the amplifiers and conditions and/or processes the detected electrochemistry and temperature sensing signals, and do so within the necessary size and power constraints. Multiple simultaneous measurements of electrolytes can be achieved by integrating a single potentiometric amplifier that is time-interleaved towards ultra-low-power operation in a small-area implementation that is well suited to exploit the rapid switching properties of scaled semiconductor processes with minimal power consumption.

Interestingly, metabolites such as lactate and glucose can generate substantial currents when interacting with the optimized enzymatic electrodes. For example, instead of employing potentiostat structures that consume excessive power at 100% duty-cycle, the electronics unit 717 can use the large currents during metabolic monitoring to operate a biofuel cell (BFC) for energy harvesting purposes. For example, a switched-capacitor DC/DC converter can be included in the electronics unit 717 to form an efficient, anatomically-miniaturized energy-extraction and conversion circuit with maximum-power-point tracking capability. For example, extracted energy can be proportional to the level of the metabolite in question. Although it is presumed that the extracted energy will not be sufficient to power the entire device 700, the DC/DC converter can be used to condition this energy in such a way as to charge an on-board battery, thereby extending the battery life of the overall device. While this biofuel cell approach is operable for relatively large metabolic concentrations, little power will be generated at small concentrations; thus, as a balance between performance and system power consumption, the potentiostats can be operated at low duty cycle for low-noise, low-current amperometric metabolic sensing only when extracted power falls below a pre-specified threshold. Such regulations can be controlled by the processing unit (e.g., microcontroller optionally coupled to a memory).

Figure 9:
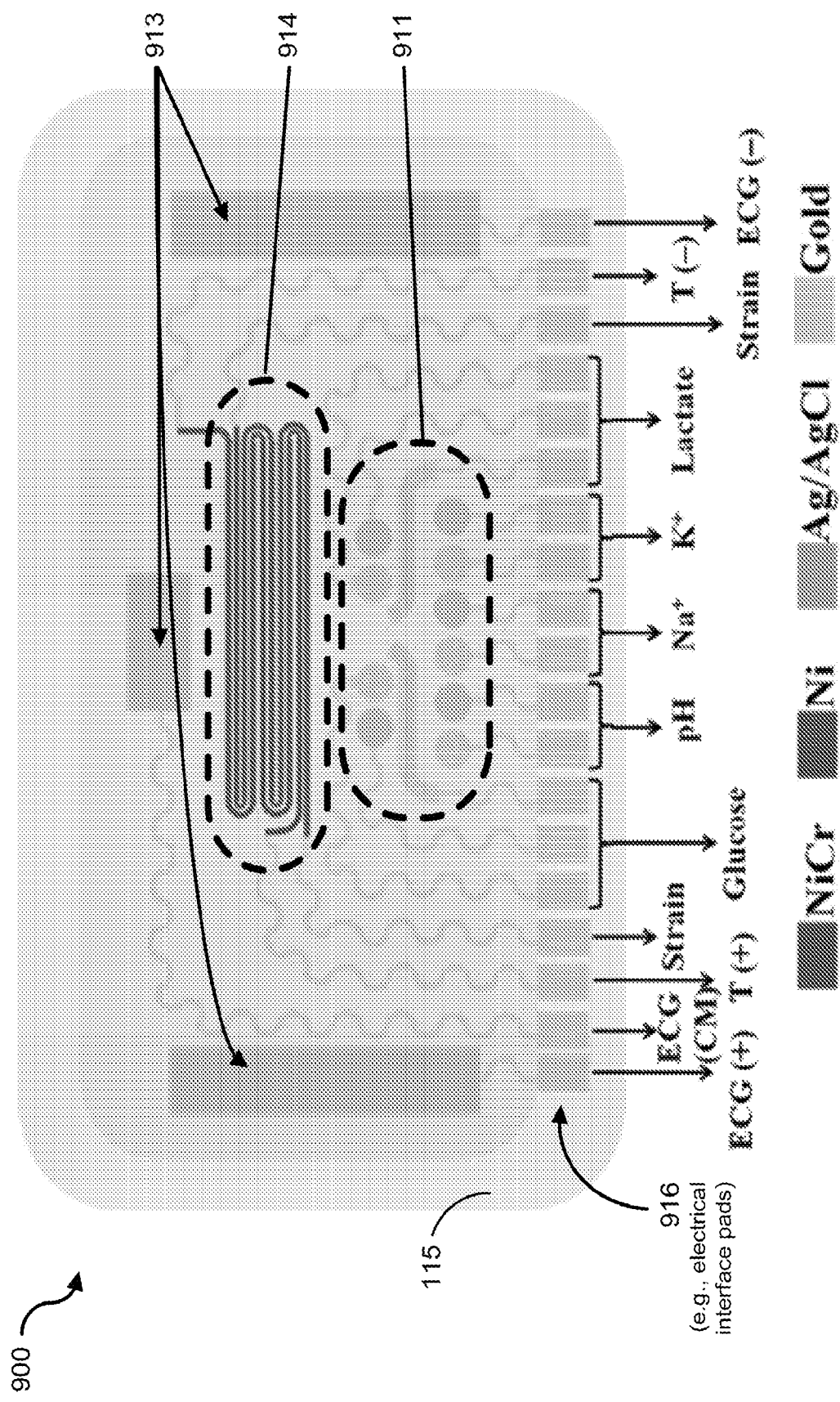
FIG. 9 shows a diagram of an example multimodal sensor device in accordance with some embodiments of the present technology.

FIG. 9 shows a diagram of an example embodiment of a FlexEM$^2$ device 900. The device 900 includes a multi-electrode electrochemical sensing module 911 and the second sensing module 113, including an electrophysiological sensing module 913 and a physical parameter sensing module 914, on the flexible substrate 115. In some embodiments, the flexible substrate 115 includes a thin, highly flexible material that conforms well with the complex three dimensional morphology of the human skin, e.g., such as Kapton. In some embodiments of the device 900, the electrochemical sensing module 911 includes one or more working electrodes coated with a biocompatible biocatalytic layer specific to a target analyte. For example, a lactate biosensor module can include a working electrode coated with Lactate Oxidase-modified Prussian Blue, and a sub-dermal glucose biosensor module can include a working electrode coated with Glucose Oxidase-modified Prussian Blue. The electrochemical sensing module 911 of the device 900 includes corresponding reference electrode(s) and/or counter electrode(s) to the respective working electrode(s), e.g., for various electrochemical sensing techniques including but not limited to amperometric measurements. In some implementations, the counter electrode(s) of the electrochemical sensing module 911 includes the functionalization coating, e.g., such as that of the working electrode. The electrodes of the electrochemical sensing module 911 are separated from electrodes of the electrophysiological sensing module 913 and a physical parameter sensing module 914. In the example device 900 shown in FIG. 9, the physical parameter sensing module 914 includes an RTD positioned on the flexible substrate 115 above the region where the electrodes of the electrochemical sensing module 911 are positioned. Also shown in FIG. 9, the device 900 includes electrodes of the electrophysiological sensing module 913 positioned at least partially around the electrode(s) of the physical parameter sensing module 914 and the electrochemical sensing module 911. In some embodiments, the electrodes of the electrophysiological sensing module 913 include Ag/AgCl electrodes; the electrodes of the electrochemical sensing module 911 include gold and Ag/AgCl electrodes; and the RTD of the physical parameter sensing module 914 includes two separate traces made of nickel and chromium, respectively, to produce temperature measurements from detection of strain, while simultaneously sensing the strain itself (e.g., for respiration monitoring). The device 900 includes an electronics unit 917 that electrically interfaces with the electrochemical sensing module 911, the electrophysiological sensing module 913 and the physical parameter sensing module 914 via electrical contacts 916. In some embodiments, some or all of the components of the electronics unit 917 are fabricated on the flexible substrate 115; whereas in some embodiments, the electronics unit 917 is independent of the flexible substrate 115 and electrically connected through interconnecting wires.

The flexible substrate 115 of the device 900 is produced by integrating thin-film processes with flexible plastic substrates and is capable to adhere and conform to the epidermis. The device 900 includes microfabricated arrays of multiple, different modes of sensor electrodes, including three epidermal solid-contact ion-selective electrodes (ISE) sets for (i) potentiometric measurements of performance-relevant sweat electrolytes (e.g., sodium, potassium and pH) and of two enzyme-based biosensors for (ii) selective amperometric monitoring of lactate and (iii) selective amperometric monitoring of glucose. The device 900 includes sensor components for skin temperature and strain monitoring, acquired by sensing changes in the thermally- and strain-sensitive resistance of a pair of microfabricated materials. Moreover, the device 900 includes electrocorticography (e.g., ECG) and alternating-current electrodermal response (AC-EDR) to be captured in a time-interleaved manner through a pair of dry-contact electrodes appropriately spaced on the epidermal patch, e.g., where a third reference electrode is also included for ECG. Heart rate, heart rate variability, R-R interval, and other ECG diagnostic information can then be digitally extracted directly from collected single-lead ECG waveforms, while respiration rate can be acquired by observing time-series changes in strain. In implementations, for example, the device 900 is worn on the chest for the most accurate ECG and respiration rate measurements; however, the device 900 can also be worn on the arm or other locations on the body.

In the example shown in FIG. 9, the sensor array of the device 900 includes five chemical sensors, two physical sensors, and a time-multiplexed electrophysiological sensor, in which each of these sensing modules are disposed on the flexible substrate 115. In some implementations, for example, the electrode sensor array is fabricated by lithography onto a flexible substrate (e.g., Kapton) for incorporation onto a band-aid-like patch that can be worn on the chest, or an armband mounted on the wearer's arm, or other body part. In some embodiments of the device 900, a removable (e.g., attachable and detachable) polyimide strip can be used for supporting the sensor array and interfacing with the patch/armband configuration. In some embodiments of the device 900, the flexible substrate 115 includes an insulating layer formed over the interconnections between the electrodes and the interfacing pads 916 that can electrically connect to the electronics unit, where the insulating layer is designed to expose certain electrodes to allow direct contact with the skin. In some embodiments of the device 900, the flexible substrate is designed to have a small area, e.g., ~30×20 mm$^2$ Kapton substrate. In some implementations, the flexible sensor array can be attached to the patch or to the armband through a double-adhesive Velcro. In some embodiments of the device 900, a microchannel gap is included around the electrode area (e.g., using proper thin spacers), which can facilitate the flux of fresh perspiration over the sensor array.

Certain electrodes of the electrochemical sensing module 911 can include a reagent layer and/or a selective membrane cocktail composition for the amperometric biosensors and for the potentiometric ISE. For example, the reagent layer can include one or more target enzymes corresponding to the target analyte to detect (e.g., lactate oxidases and/or glucose oxidase and/or dehydrogenases), an enzyme stabilizer, redox mediators, cross-linking agent and/or a biocompatible 'host' overlayer (e.g., chitosan, Nafion). The reagent layer for the electrolyte (ISE) sensors can incorporate the corresponding ionophore (e.g., receptor) within a polyvinyl chloride (PVC) host matrix, containing a suitable plasticizer. The composition of the specific reagent layers are tailored to meet the target response characteristics. To facilitate mass production, for example, such low-volume reagent layers can be dispersed rapidly and reproducibly via ink jet. For example, the quality of the microfabrication and reagent-dispersion processes can be assessed by examining the sensor-to-sensor and array-to-array reproducibility (using the same printing batch or different batches).

The device 900 provides structural resiliency to withstand essential for continuous epidermal wear. Enduring repetitive mechanical deformations and accommodating day-to-day activity is an important attribute of robust, continuously-wearable epidermal sensors. The relevant mechanical stress (e.g., expected during normal activity) is a factor upon the sensor performance with the epidermis. Example implementations of the device 900 addresses the effect of various mechanical strain permutations, including repeated bending (of different curvatures), stretching, pinching, twisting, etc. upon the structural resiliency, electrical properties and response. The strain/temperature gauge, for example, is designed based on the mechanism of strain- and temperature-induced resistance change of metallic conductors (resistance temperature detector, or RTD). For example, the peak strain experienced by a metallic conductor under bending conditions is given by the following equation (Eq. 1):

$$\varepsilon = \frac{d_s + d_f}{2r} \times 100\% \quad (1)$$

where $\varepsilon$ is the peak strain, $d_f$ is the thickness of the conductor, $d_s$ is the thickness of the substrate, and r is the radius of curvature. Conductor strain then leads to a change in resistance, calibrated by the following equation (Eq. 2):

$$GF = \frac{\Delta R/R}{\varepsilon} \quad (2)$$

where Gauge Factor (GF) is defined as the ratio of relative change in electrical resistance R. Thus, continuous measurement of the strain gauge resistance enables inference of the resulting strain, which given the sensor dimensions, can be used to infer the underlying muscle movement. Time-series derivatives can then be employed to infer muscle acceleration, respiration rates, and other parameters.

Among the possible conductor material choices for the strain gauge, for example, nickel can be initially employed over gold and copper (e.g., two traditionally-used conductors). For example, it has a 50% larger thermal coefficient of resistance, and it has up to 30× larger resistance, thereby easing the effects of parasitic lead resistance that may otherwise interfere with measurement accuracy. In some implementations, for example, elastomers can be used as strain gauge elements (e.g., carbon-black-doped PDMS). Since strain gauges/RTDs also respond to temperature changes, a separate strain sensor can be fabricated using a different material (e.g., chromium) in order to dynamically compensate for temperature effects. For example, this can provide an inherent temperature sensor that can be explicitly used in the device 900.

Figure 10A:
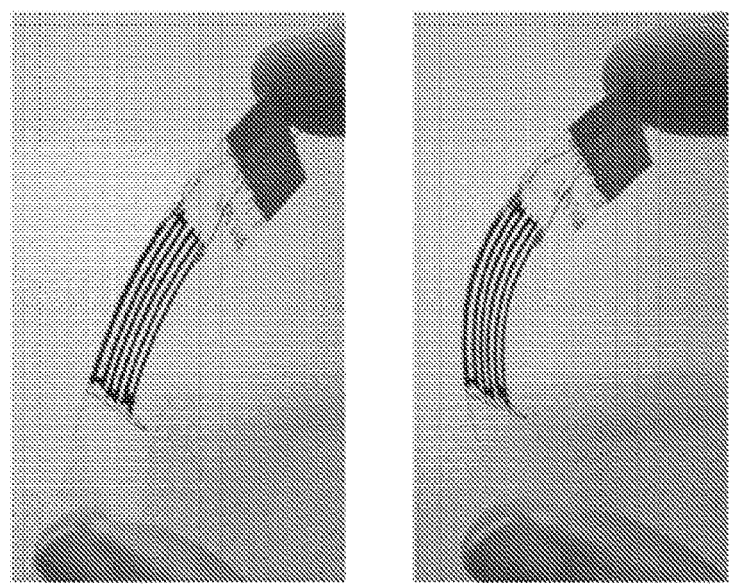
FIGS. 10A and 10B show images of an example strain gauge and a graph of example measurement results.
Figure 10B:
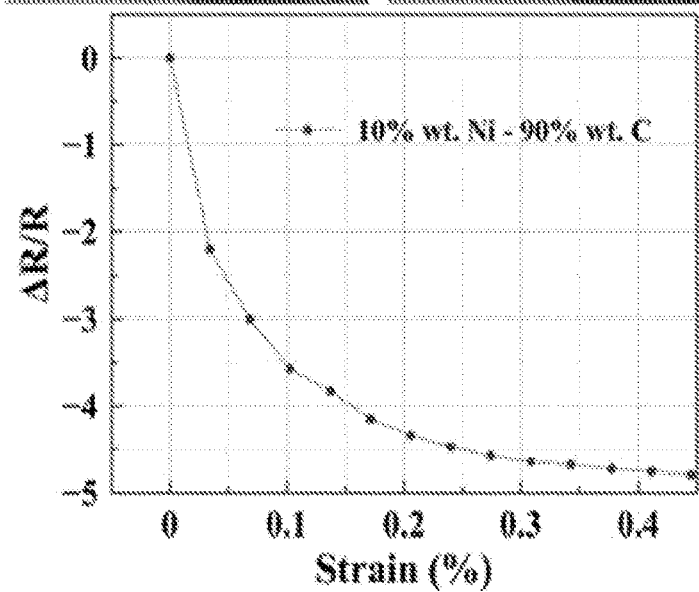

For example, to validate the example strain measurement module, a batch of example strain gauges using a 10% nickel/90% carbon printable ink were fabricated, as shown in the images of FIG. 10A. As shown by these images, the strain gauge exhibits more than sufficient radius of curvature and can be easily integrated onto a wearable patch for conformal skin contact. FIG. 10B shows a graph indicating example results that strain provides a sufficiently large change in resistance for measurement by ultra-low-power electronics devices.

Figure 11:
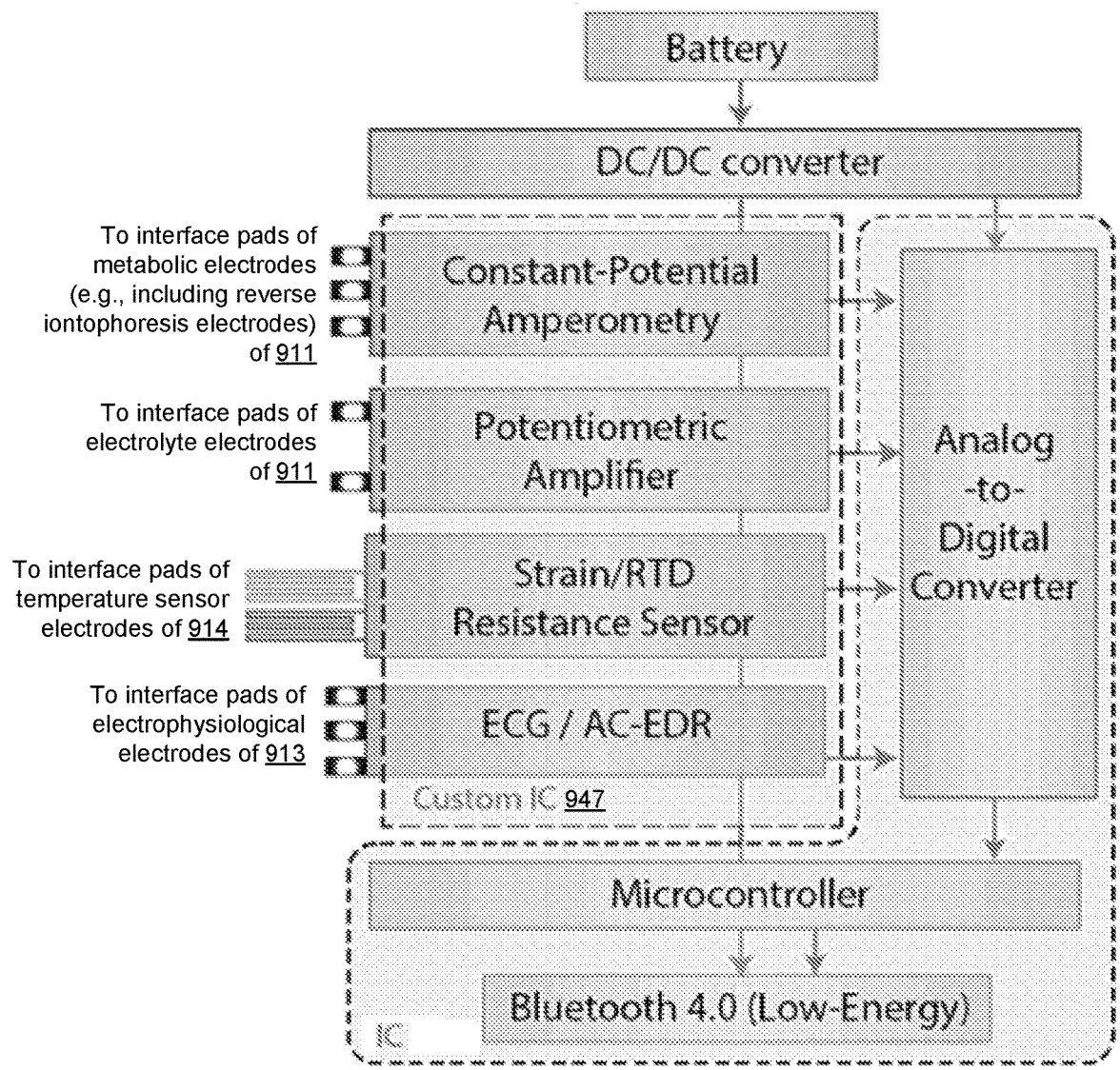
FIG. 11 shows a block diagram of an example electronics unit to electrically interface with the sensors of the example device of FIG. 9.

FIG. 11 shows a block diagram of an example electronics unit 917 to electrically interface with the sensors of the device 900. The electronics unit 917 includes amplifiers and current injectors for metabolic electrodes (e.g., including constant-potential amperometry and/or reverse iontophoresis), potentiometric amplifier, and a resistance temperature detector (RTD) temperature/strain monitor, which meet size constraints (e.g., of or less than 2 mm$^2$) and total power consumption specifications (e.g., of or less than 100 μW) for the described example wearable monitoring applications. The electronics unit 917 can include a customized integrated circuit (IC) 947, e.g., on a single microchip, that includes the amplifiers and conditions and/or processes the detected electrochemistry and temperature sensing signals (e.g., time-interleaved ECG/AC-EDR amplifier/drivers, potentiometric arrays, amperometric arrays, and resistance temperature detector (RTD) temperature/strain monitors), which is within the necessary size and power constraints. The electronics unit 917 includes a wireless transceiver, analog-to-digital converter, and data processing unit (e.g., a microprocessor, which can be coupled to a memory). Multiple simultaneous measurements of electrolytes can be achieved by integrating a single potentiometric amplifier that is time-interleaved towards ultra-low-power operation in a small-area implementation that is well suited to exploit the rapid switching properties of scaled semiconductor processes with minimal power consumption.

In some implementations, for example, the electronics unit 917 can measure the electrolytes by integrating time-multiplexed potentiometric amplifiers optimized for ultra-low-power operation in an anatomically miniaturized form factor. Measurement of metabolites can be operated by constant-potential amperometry, and/or fast scan cyclic voltammetry (FSCV) techniques, which has excellent analyte-specificity, can be performed. Constant-potential amperometry can include time-multiplexed potentiostats for voltage control of the enzymatic electrodes. Current transduction can employ a capacitive-charging time-to-digital ADC solution that exploits the inherent high-speed, high-density properties of deep-submicron CMOS technologies, resulting in a design with minimal on-chip area and ultra-low-power operation. An example advantage of constant-potential amperometry, that is, the lack of changing bias points, can help bias the biopotential (ECG) amplifier. For example, the power consumption of the device 900 can be approximately 50 μW per amperometric channel and 25 μW per potentiometric channel, e.g., including all necessary support circuitry. Notably, for example, this capability surpasses the capabilities of conventional wearable sensor devices.

Measurement of ECG and AC-EDR can utilize the same two electrodes in a time-interleaved fashion in order to save electrode area and minimize the overall size of the device footprint. AC-GSR is an excellent indicator of an individual's stress level (e.g., whose DC-GSR counterpart is used in lie-detector tests), and does not have to be measured frequently (e.g., once per minute is often sufficient). As a result, ECG is captured from electrodes the vast majority of the time. In some implementations, for example, the on-chip ECG amplifier can use low-noise, low-power instrumentation techniques such as sizing differential input pair transistors in subthreshold while sizing others for above threshold operation, employing MOS-bipolar pseudo resistors for high-resistance biasing, and employing a current re-use topology. Alternatively, for example, AC-EDR can employ frequency spectroscopy using a switched-capacitor DAC-generated chirp signal ranging from 0-100 kHz followed by a transimpedance amplifier for readout based on a switched capacitor. The example strain/RTD sensing can include using the AC-EDR DAC and transimpedance amplifier for the creation of precise DC voltages followed by current transduction, RC-based delay quantization, and more traditional current-source/instrumentation amplifier-based techniques In some implementations including those where metabolites such as lactate and glucose are measured, the device 900 can employ a BFC to power at least some of the components of the electronics unit 917. For example, such metabolites can generate substantial currents when interacting with the optimized enzymatic electrodes. For example, instead of employing potentiostat structures that consume excessive power at 100% duty-cycle, the electronics unit 917 can use the large currents during metabolic monitoring to operate the BFC for energy harvesting purposes. For example, a switched-capacitor DC/DC converter can be included in the electronics unit 917 to form an efficient, anatomically-miniaturized energy-extraction and conversion circuit with maximum-power-point tracking capability. For example, extracted energy can be proportional to the level of the metabolite in question. For example, the DC/DC converter can be used to condition the extracted energy in such a way as to charge an on-board battery, thereby extending the battery life of the overall device. While this biofuel cell approach is operable for relatively large metabolic concentrations, little power will be generated at small concentrations; thus, as a balance between performance and system power consumption, the potentiostats can be operated at low duty cycle for low-noise, low-current amperometric metabolic sensing only when extracted power falls below a pre-specified threshold. Such regulations can be controlled by the processing unit (e.g., microcontroller optionally coupled to a memory).

Figure 12:
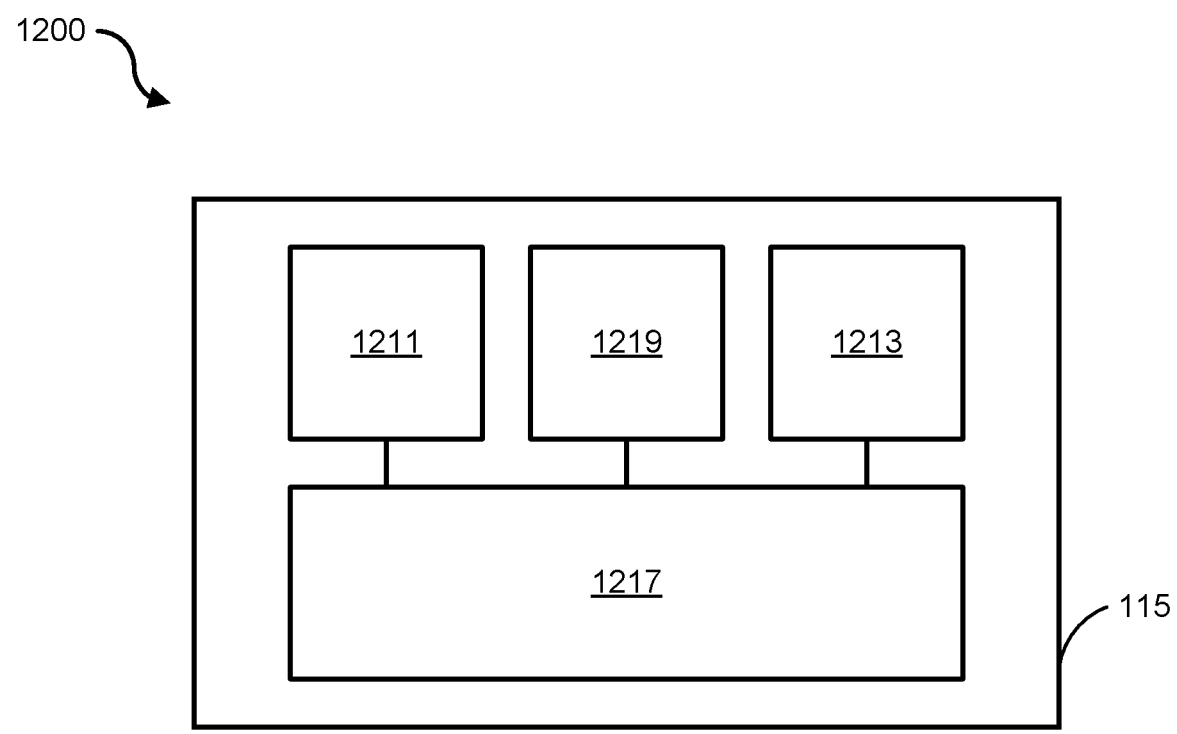
FIG. 12 shows a diagram of an example multimodal sensor device.

FIG. 12 shows a diagram of an example multimodal sensor device 1200 integrated with an electrochemical sensing module 1211, a second sensing module 1213 (e.g., an electrophysiological sensing module and/or a physical parameter sensing module), and a biofuel cell module 1219 on the flexible substrate 115 and electrically connected to an electronics unit 1217. Embodiments of the multimodal sensor device 1200 include the example embodiments of the Chem-Phys device 200, the device 700 and the device 900. The electrochemical sensing module 1211 of the multimodal sensor device 1200 is electrically interfaced with the biofuel cell module 1219 via the electronics unit 1219, which can comprise an electrical circuit including a DC/DC converter that tracks the power coming from the biofuel cell module 1219, e.g., which is related to the underlying analyte concentration for sensing by the electrochemical sensing module 1211, to achieve self- or quasi-self-powered operation of the multimodal sensor device 1200. The example integrated multimodal biosensor-biofuel cell and electronics device platform of the device 1200 can include discrete component based devices and interfacing, e.g., including the design of electronics for an anatomically-miniaturized electrochemical analyzer and the associated electronic interfaces, digitization circuitry, and communications. Example embodiments of the electronics unit 1219 can include the embodiments described for the electronics unit 717 and the electronics unit 917.

In some embodiments of the biofuel cell module 1219, for example, the biofuel cell module 1219 is structured to include an anode disposed on the flexible substrate 115 that includes an electrically conductive material. The anode includes a fuel cell catalyst to facilitate the conversion of a fuel substance in the fluid (e.g., sweat) to a first product in an oxidative process that releases electrons captured at the anode, thereby extracting energy from the fuel substance. The biofuel cell module 1219 includes a cathode disposed on the flexible substrate 115 adjacent to and separated from the anode, the cathode including a material that is electrically conductive and capable of reducing an oxygenated substance in the fluid to a second product in a chemical reduction process in which the second product gains electrons. The biofuel cell module 1219 is electrically coupled to the electronics unit 1217, which is electrically coupled to the electrochemical sensing module 1211, such that, the electronics unit 1217 is operable to obtain the extracted energy as electrical energy from the biofuel cell module 1219 and to supply the electrical energy to the electrochemical sensing module 1211.

In some embodiments, for example, the biofuel cell module 1219 can include the fuel cell catalyst encased on the surface of the anode in a porous scaffold structure formed of a conducting polymer. For example, the fuel cell catalyst can include Lactate oxidase (LOx), Glucose oxidase (GOx), or uricase, among others. For example, the conducting polymer can include polyaniline, polypyrrole, polythiophene, poly(3, 4-ethylenedioxythiophene), poly(p-phenylene sulfide), polyfluorine, polyphenylene, polypyrene, polyazulene, polynaphthalene, poly(acetylene), poly(p-phenylene vinylene), and/or polyphenyldiamine. In some embodiments of the biofuel cell module 1219, the fuel cell catalyst is entrapped in a selectively permeable membrane coupled to the surface of the anode. For example, the permeable-selective membrane can include Nafion and/or chitosan. In some embodiments of the biofuel cell module 1219, the fuel cell catalyst is electrostatically or covalently bound to the surface of the anode. In some embodiments, for example, the anode is structured to include an electroactive mediator to facilitate electron transfer between an active site of the fuel cell catalyst and the surface of the anode.

Some examples of the biofuel cell module 1219 are described in U.S. Patent Publication No. 2016/0338626A1, which is incorporated by reference in its entirety for all purposes.

EXAMPLES

In some embodiments in accordance with the present technology (example A1), a multimodal sensor device includes a flexible substrate including an electrically insulative material and structured to adhere to a user; an electrochemical sensor including a first electrode disposed on the substrate, in which the first electrode includes a surface including a chemical substance that includes a catalyst or a reactant corresponding to an analyte in a fluid, and a second electrode disposed on the substrate separated from the first electrode, the first and second electrodes operable to measure an electrical signal corresponding to a redox reaction including the chemical substance and analyte at the electrochemical sensor; and an electrophysiological sensor including two or more electrodes disposed on the substrate to acquire an electrophysiological signal of the user, in which, when the device is electrically coupled to an electronics unit and adhered to the user, the device is operable to simultaneously monitor an electrochemical parameter and an electrophysiological parameter of the user.

Example A2 includes the device of example A1, in which the electrochemical sensor further includes a reference electrode positioned between the first and the second electrodes on the substrate and having a surface including the chemical substance, in which the first electrode is operable as a working electrode and the second electrode is operable as a counter electrode for amperometry measurements by the electrochemical sensor.

Example A3 includes the device of example A2, in which the electrochemical sensor is configured to detect lactate from perspiration and the electrophysiological sensor is configured to detect electrocardiogram (ECG).

Example A4 includes the device of example A3, further including a second electrochemical sensor including a second working electrode disposed on the substrate, a second counter or reference electrode disposed on the substrate separated from the second working electrode, and a reverse iontophoretic electrode that at least partially encompasses the second working electrode and the second counter or reference electrode, in which the reverse iontophoretic electrode is operable to apply an electric field to drive ion flow from interstitial fluid (ISF) toward the second working electrode and the second counter or reference electrode, and in which the second working electrode includes a surface including a second chemical substance that includes a second catalyst or a second reactant corresponding to a subdermal analyte present in the ISF of the user, in which the second electrochemical sensor is operable to measure an electrical signal corresponding to a second redox reaction including the second chemical substance and subdermal analyte at the second electrochemical sensor simultaneously with sensing the electrochemical parameter and the electrophysiological parameter of the user.

Example A5 includes the device of example A4, in which the subdermal analyte includes glucose.

Example A6 includes the device of example A2, further including an electrolyte electrochemical sensor including one or more electrolyte working electrodes disposed on the substrate and one or more electrolyte counter/reference electrodes each disposed on the substrate separated from the corresponding electrolyte working electrode, in which the electrolyte electrochemical sensor is operable to detect a target electrolyte in contact with the electrolyte electrochemical sensor simultaneously with sensing the electrochemical parameter and the electrophysiological parameter of the user.

Example A7 includes the device of example A6, in which the one or more electrolyte working electrodes and the one or more electrolyte counter/reference electrodes are operable to detect the target electrolyte using cyclic voltammetry.

Example A8 includes the device of example A2, further including a physical parameter sensor on the substrate to measure at least one of temperature or respiration rate, or strain simultaneously with sensing the electrochemical parameter and the electrophysiological parameter of the user.

Example A9 includes the device of example A1, in which the device includes the electronics unit electrically coupled to the electrochemical sensor and the electrophysiological sensor via electrical interconnects, the electronics unit configured to supply electrical energy to the electrochemical sensor.

Example A10 includes the device of example A1, in which the electronics unit includes a signal conditioning circuit to amplify detected signals including the electrical signal measured by the electrochemical sensor and the electrophysiological signal acquired by the electrophysiological sensor, a data processing unit including a processor to process data based on the measured electrical signal and acquired electrophysiological signal, and a memory to store or buffer the data, and a wireless communications unit to wirelessly transmit the processed signals to an external device.

Example A11 includes the device of example A10, in which the electronics unit includes a printed circuit board (PCB) including a potentiostat, an analog front-end (AFE) unit, and a RF radio unit for wireless telemetry of the results to a mobile device.

Example A12 includes the device of example A10, in which the mobile device includes a smartphone, a smartwatch, a smartglasses, or a computer including a laptop or desktop.

Example A13 includes the device of example A10, in which the RF radio unit includes a Bluetooth Low-Energy (BLE) chipset.

Example A14 includes the device of example A1, in which the surface of the first electrode is structured to include the chemical substance immobilized on the first electrode surface by electropolymeric entrapment in a polymer film or selectively permeable scaffold.

Example A15 includes the device of example A14, in which the polymer film includes poly(o-phenylenediamine).

Example A16 includes the device of example A14, in which the selectively permeable scaffold includes Nafion or chitosan.

Example A17 includes the device of example A1, in which the electrophysiological sensor further includes a second detecting electrode configured at a second location on the substrate to acquire a second electrophysiological signal of the user as a reference signal to the electrophysiological signal.

Example A18 includes the device of example A1, in which the electrodes of the electrochemical sensor are separated from the electrodes of the electrophysiological sensor via a hydrophobic layer.

Example A19 includes the device of example A1, further including a biofuel cell module disposed on the substrate and operable to electrochemically extract energy from the fluid to provide power to the device, the biofuel cell including an anode disposed on the substrate and including an electrically conductive material, the anode including a fuel cell catalyst to facilitate the conversion of a fuel substance in the fluid to a first product in an oxidative process that releases electrons captured at the anode, thereby extracting energy from the fuel substance, and a cathode disposed on the substrate adjacent to and separated from the anode, the cathode including a material that is electrically conductive and capable of reducing an oxygenated substance in the fluid to a second product in a chemical reduction process in which the second product gains electrons, in which the biofuel cell is electrically coupled to the electronics unit that is electrically coupled to the electrochemical sensor, such that, the electronics unit is operable to obtain the extracted energy as electrical energy from the biofuel cell and to supply the electrical energy to the electrochemical sensor of the device.

Example A20 includes the device of example A19, in which the fuel cell catalyst includes one or both of lactate oxidase (LOx) and glucose oxidase (GOx).

Example A21 includes the device of example A1, in which the device is a non-invasive, epidermal device.

In some embodiments in accordance with the present technology (example A22), a multimodal health monitoring system includes a multimodal sensor device attachable to skin of a user and a wireless receiver device. The multimodal sensor device is structured to include a flexible substrate including an electrically insulative material and structured to adhere to the user, an electrochemical sensor including a first electrode disposed on the substrate, in which the first electrode includes a surface including a chemical substance that includes a catalyst or a reactant corresponding to an analyte in a fluid of the user, and a second electrode disposed on the substrate separated from the first electrode, the first and second electrodes operable to measure an electrical signal corresponding to a redox reaction including the chemical substance and analyte at the electrochemical sensor, an electrophysiological sensor including two or more electrodes disposed on the substrate and operable to acquire an electrophysiological signal of the user, and an electronics unit, including a signal conditioning circuit to amplify detected signals including the electrical signal measured by the electrochemical sensor and the electrophysiological signal acquired by the electrophysiological sensor, and a wireless communications unit to wirelessly transmit the amplified signals to an external device, in which the multimodal sensor device is operable to simultaneously monitor an electrochemical parameter and an electrophysiological parameter of the user. The wireless receiver device is operable to receive the wirelessly transmitted signals from the multimodal sensor device.

Example A23 includes the system of example A22, in which the electronics unit includes a data processing unit including a processor to process data based on the amplified detected signals, and a memory to store or buffer the data.

Example A24 includes the system of example A23, in which the electronics unit includes a printed circuit board (PCB) including a potentiostat, an analog front-end (AFE) unit, and a RF radio unit for wireless telemetry of the amplified signals to the wireless receiver device.

Example A25 includes the system of example A24, in which the RF radio unit includes a Bluetooth Low-Energy (BLE) chipset.

Example A26 includes the system of example A22, in which the wireless receiver device includes a mobile device including a smartphone, a smartwatch, a smartglasses, or a computer including a laptop or desktop.

Example A27 includes the system of example A26, in which the mobile device includes a software application operable on the mobile device and comprising instructions stored in a memory and processed by a processor of the mobile device, the mobile device including a wireless communications unit to receive the wirelessly transmitted signals from the multimodal sensor device.

Example A28 includes the system of example A22, further including one or more computers in communication with the wireless receiver device over the Internet, the one or more computers including a memory to store data received from the wireless receiver device associated with the detected signals, and a processor to process the received data.

Example A29 includes the system of example A22, in which the surface of the first electrode is structured to include the chemical substance immobilized on the first electrode surface by electropolymeric entrapment in a polymer film or selectively permeable scaffold.

Example A30 includes the system of example A22, in which the multimodal sensor device further includes a biofuel cell module disposed on the substrate and operable to electrochemically extract energy from the fluid to provide power to the multimodal sensor device, in which the biofuel cell is structured to include an anode disposed on the substrate and including an electrically conductive material, the anode including a fuel cell catalyst to facilitate the conversion of a fuel substance in the fluid to a first product in an oxidative process that releases electrons captured at the anode, thereby extracting energy from the fuel substance, and a cathode disposed on the substrate adjacent to and separated from the anode, the cathode including a material that is electrically conductive and capable of reducing an oxygenated substance in the fluid to a second product in a chemical reduction process in which the second product gains electrons, in which the biofuel cell is electrically coupled to the electronics unit that is electrically coupled to the electrochemical sensor, such that, the electronics unit is operable to obtain the extracted energy as electrical energy from the biofuel cell and to supply the electrical energy to the electrochemical sensor of the multimodal sensor device.

Example A31 includes the system of example A22, in which the electrochemical sensor further includes a reference electrode positioned between the first and the second electrodes on the substrate and having a surface including the chemical substance, in which the first electrode is operable as a working electrode and the second electrode is operable as a counter electrode for amperometry measurements by the electrochemical sensor.

Example A32 includes the system of example A31, in which the multimodal sensor device further includes a second electrochemical sensor including a second working electrode disposed on the substrate, a second counter or reference electrode disposed on the substrate separated from the second working electrode, and a reverse iontophoretic electrode that at least partially encompasses the second working electrode and the second counter or reference electrode, in which the reverse iontophoretic electrode is operable to apply an electric field to drive ion flow from interstitial fluid (ISF) toward the second working electrode and the second counter or reference electrode, and in which the second working electrode includes a surface including a second chemical substance that includes a second catalyst or a second reactant corresponding to a subdermal analyte present in the ISF of the user, in which the second electrochemical sensor is operable to measure an electrical signal corresponding to a second redox reaction including the second chemical substance and subdermal analyte at the second electrochemical sensor simultaneously with sensing the electrochemical parameter and the electrophysiological parameter of the user.

Example A33 includes the system of example A31, in which the multimodal sensor device further includes an electrolyte electrochemical sensor including one or more electrolyte working electrodes disposed on the substrate and one or more electrolyte counter/reference electrodes each disposed on the substrate separated from the corresponding electrolyte working electrode, in which the electrolyte electrochemical sensor is operable to detect a target electrolyte in contact with the electrolyte electrochemical sensor simultaneously with sensing the electrochemical parameter and the electrophysiological parameter of the user.

Example A34 includes the system of example A31, in which the multimodal sensor device further includes a physical parameter sensor on the substrate to measure at least one of temperature or respiration rate, or strain simultaneously with sensing the electrochemical parameter and the electrophysiological parameter of the user.

Example A35 includes the system of example A22, in which the electrophysiological sensor further includes a second detecting electrode configured at a second location on the substrate to acquire a second electrophysiological signal of the user as a reference signal to the electrophysiological signal.

Example A36 includes the system of example A22, in which the electrodes of the electrochemical sensor are separated from the electrodes of the electrophysiological sensor via a hydrophobic layer.

Example A37 includes the system of example A22, in which the electronics unit is configured to supply electrical energy to the electrochemical sensor.

In some embodiments in accordance with the present technology (example A38), a method to simultaneously monitor an electrochemical parameter and an electrophysiological parameter of a user includes: detecting, at electrodes of an electrochemical sensor disposed on a flexible substrate adhered to skin of the user, a first electrical signal produced as a result of a redox reaction involving an analyte in a fluid of the user and a chemical substance coupled to an electrode of the electrochemical sensor; detecting, at electrodes of an electrophysiological sensor disposed on the flexible substrate adhered to the skin of the user, a second electrical signal associated with an electrophysiological signal of the user, in which the detecting the first electrical signal and the second electrical signal occurs simultaneously; amplifying, at an electronics unit, the first electrical signal detected by the electrochemical sensor and the second electrical signal detected by the electrophysiological sensor; and wirelessly transmitting, at the electronics unit, the first electrical signals and second electrical signal to an external device.

Example A39 includes the method of example A38, further including processing the first electrical signal and second electrical signal as digital data, and a memory to store or buffer the digital data.

Example A40 includes the method of example A38, further including extracting electrical energy, at anode and cathode electrodes of a biofuel cell disposed on the flexible substrate, from a fuel substance present in the fluid by converting the fuel substance to a first product in an oxidative process that releases electrons captured at the anode and reducing an oxygenated substance in the fluid to a second product in a chemical reduction process in which the second product gains electrons at the cathode; obtaining, at the electronics unit, the extracted electrical energy; and supplying, by the electronics unit, the extracted electrical energy to the electrochemical sensor.

Example A40 includes the method of example A38, in which the method is performed using any of the devices of claims 1-21.

In some embodiments in accordance with the present technology (example B1), a wearable, real-time sensing device for simultaneous monitoring electrochemical, electrophysiological and physical parameters in a subject is disclosed. The device includes two or more sensing modalities fabricated on a flexible substrate.

Example B2 includes the device of example B1, in which the device is a non-invasive, epidermal device.

Example B3 includes the device of example B1, in which the sensing modality includes a three-electrode amperometric lactate biosensor and a bipolar ECG sensor.

Example B4 includes the device of example B3, in which the three amperometric electrodes are separated from the Ag/AgCl ECG electrodes via a printed hydrophobic layer to maximize sensor stability and signal-to-noise ratio.

Example B5 includes the device of example B3, in which the two sensors are interfaced to a custom printed circuit board (PCB) featuring a potentiostat, an ECG analog front-end (AFE), and a Bluetooth Low-Energy (BLE) radio for wireless telemetry of the results to a mobile platform, such as a smartphone or laptop.

In some embodiments in accordance with the present technology (example B6), a method of real-time monitoring the health and fitness of a subject by using the device of any one of examples B1-B5.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A multimodal sensor device, comprising:
a flexible substrate including an electrically insulative material and structured to adhere to a user;
an electrochemical sensor comprising a first electrode disposed on the substrate, wherein the first electrode includes a surface including a chemical substance that includes a catalyst for an analyte in a fluid, and a second electrode disposed on the substrate separated from the first electrode, the first and second electrodes operable to measure an electrical signal corresponding to a redox reaction including the chemical substance and analyte at the electrochemical sensor; and
an electrophysiological sensor comprising two or more electrodes disposed on the substrate to acquire an electrophysiological signal of the user,
wherein, when the device is electrically coupled to an electronics unit and adhered to the user, the electrochemical sensor is operable to monitor an electrochemical parameter of the user, and, at the same time, the electrophysiological sensor is operable to monitor an electrophysiological parameter of the user.

2. The device of claim 1, wherein the electrochemical sensor further comprises a reference electrode positioned between the first and the second electrodes on the substrate and having a surface including the chemical substance, wherein the first electrode is operable as a working electrode and the second electrode is operable as a counter electrode for amperometry measurements by the electrochemical sensor.

3. The device of claim 2, wherein the electrochemical sensor is configured to detect lactate from perspiration and the electrophysiological sensor is configured to detect electrocardiogram (ECG).

4. The device of claim 3, further comprising:
a second electrochemical sensor comprising a second working electrode disposed on the substrate, a second counter or reference electrode disposed on the substrate separated from the second working electrode, and a reverse iontophoretic electrode that at least partially encompasses the second working electrode and the second counter or reference electrode, wherein the reverse iontophoretic electrode is operable to apply an electric field to drive ion flow from interstitial fluid (ISF) toward the second working electrode and the second counter or reference electrode, and wherein the second working electrode includes a surface including a second chemical substance that includes a second catalyst for a subdermal analyte present in the ISF of the user,
wherein the second electrochemical sensor is operable to measure an electrical signal corresponding to a second redox reaction including the second chemical substance and subdermal analyte at the second electrochemical sensor simultaneously with sensing the electrochemical parameter and the electrophysiological parameter of the user.

5. The device of claim 4, wherein the subdermal analyte includes glucose.

6. The device of claim 2, further comprising:
an electrolyte electrochemical sensor comprising one or more electrolyte working electrodes disposed on the substrate and one or more electrolyte counter/reference electrodes each disposed on the substrate separated from the corresponding electrolyte working electrode,
wherein the electrolyte electrochemical sensor is operable to detect a target electrolyte in contact with the electrolyte electrochemical sensor simultaneously with sensing the electrochemical parameter and the electrophysiological parameter of the user.

7. The device of claim 6, wherein the one or more electrolyte working electrodes and the one or more electrolyte counter/reference electrodes are operable to detect the target electrolyte using cyclic voltammetry.

8. The device of claim 2, further comprising:
a physical parameter sensor on the substrate to measure at least one of temperature or respiration rate, or strain simultaneously with sensing the electrochemical parameter and the electrophysiological parameter of the user.

9. The device of claim 1, wherein the electronics unit includes:
a signal conditioning circuit to amplify detected signals including the electrical signal measured by the electrochemical sensor and the electrophysiological signal acquired by the electrophysiological sensor,
a data processing unit including a processor to process data based on the measured electrical signal and acquired electrophysiological signal, and a memory to store or buffer the data, and
a wireless communications unit to wirelessly transmit the processed signals to an external device.

10. The device of claim 1, wherein the surface of the first electrode is structured to include the chemical substance immobilized on the first electrode surface by electropolymeric entrapment in a polymer film or selectively permeable scaffold.

11. The device of claim 10, wherein the polymer film includes poly(o-phenylenediamine), and wherein the selectively permeable scaffold includes Nafion or chitosan.

12. The device of claim 1, wherein the electrophysiological sensor further includes a second detecting electrode configured at a second location on the substrate to acquire a second electrophysiological signal of the user as a reference signal to the electrophysiological signal.

13. The device of claim 1, wherein the electrodes of the electrochemical sensor are separated from the electrodes of the electrophysiological sensor via a hydrophobic layer.

14. The device of claim 1, further comprising:
a biofuel cell module disposed on the substrate and operable to electrochemically extract energy from the fluid to provide power to the device, the biofuel cell comprising:
an anode disposed on the substrate and including an electrically conductive material, the anode including a fuel cell catalyst to facilitate the conversion of a fuel substance in the fluid to a first product in an oxidative process that releases electrons captured at the anode, thereby extracting energy from the fuel substance, and
a cathode disposed on the substrate adjacent to and separated from the anode, the cathode including a material that is electrically conductive and capable of reducing an oxygenated substance in the fluid to a second product in a chemical reduction process in which the second product gains electrons,
wherein the biofuel cell is electrically coupled to the electronics unit that is electrically coupled to the electrochemical sensor, such that, the electronics unit is operable to obtain the extracted energy as electrical energy from the biofuel cell and to supply the electrical energy to the electrochemical sensor of the device.

15. A multimodal health monitoring system, comprising:
multimodal sensor device attachable to skin of a user and structured to include:
a flexible substrate including an electrically insulative material and structured to adhere to the user,
an electrochemical sensor including a first electrode disposed on the substrate, wherein the first electrode includes a surface including a chemical substance that includes a catalyst for an analyte in a fluid of the user, and a second electrode disposed on the substrate separated from the first electrode, the first and second electrodes operable to measure an electrical signal corresponding to a redox reaction including the chemical substance and analyte at the electrochemical sensor,
an electrophysiological sensor comprising two or more electrodes disposed on the substrate and operable to acquire an electrophysiological signal of the user, and
an electronics unit, including a signal conditioning circuit to amplify detected signals including the electrical signal measured by the electrochemical sensor and the electrophysiological signal acquired by the electrophysiological sensor, and a wireless communications unit to wirelessly transmit the amplified signals to an external device,
wherein the electrochemical sensor is operable to monitor an electrochemical parameter of the user, and, and at the same time, the electrophysiological sensor is operable to monitor an electrophysiological parameter of the user; and
a wireless receiver device to receive the wirelessly transmitted signals from the multimodal sensor device.

16. The system of claim 15, wherein the electrochemical sensor further comprises a reference electrode positioned between the first and the second electrodes on the substrate and having a surface including the chemical substance, wherein the first electrode is operable as a working electrode and the second electrode is operable as a counter electrode for amperometry measurements by the electrochemical sensor.

17. The system of claim 16, wherein the multimodal sensor device further comprises:
a second electrochemical sensor comprising a second working electrode disposed on the substrate, a second counter or reference electrode disposed on the substrate separated from the second working electrode, and a reverse iontophoretic electrode that at least partially encompasses the second working electrode and the second counter or reference electrode, wherein the reverse iontophoretic electrode is operable to apply an electric field to drive ion flow from interstitial fluid (ISF) toward the second working electrode and the second counter or reference electrode, and wherein the second working electrode includes a surface including a second chemical substance that includes a second catalyst for a subdermal analyte present in the ISF of the user,
wherein the second electrochemical sensor is operable to measure an electrical signal corresponding to a second redox reaction including the second chemical substance and subdermal analyte at the second electrochemical sensor simultaneously with sensing the electrochemical parameter and the electrophysiological parameter of the user.

18. The system of claim 16, wherein the multimodal sensor device further comprises:
an electrolyte electrochemical sensor comprising one or more electrolyte working electrodes disposed on the substrate and one or more electrolyte counter/reference electrodes each disposed on the substrate separated from the corresponding electrolyte working electrode, wherein the electrolyte electrochemical sensor is operable to detect a target electrolyte in contact with the electrolyte electrochemical sensor simultaneously with sensing the electrochemical parameter and the electrophysiological parameter of the user.

19. The system of claim 16, wherein the multimodal sensor device further comprises:
a physical parameter sensor on the substrate to measure at least one of temperature or respiration rate, or strain simultaneously with sensing the electrochemical parameter and the electrophysiological parameter of the user.

20. The system of claim 15, wherein the multimodal sensor device further includes:
a biofuel cell module disposed on the substrate and operable to electrochemically extract energy from the fluid to provide power to the multimodal sensor device, wherein the biofuel cell is structured to include:
an anode disposed on the substrate and including an electrically conductive material, the anode including a fuel cell catalyst to facilitate the conversion of a fuel substance in the fluid to a first product in an oxidative process that releases electrons captured at the anode, thereby extracting energy from the fuel substance, and
a cathode disposed on the substrate adjacent to and separated from the anode, the cathode including a material that is electrically conductive and capable of reducing an oxygenated substance in the fluid to a second product in a chemical reduction process in which the second product gains electrons,
wherein the biofuel cell is electrically coupled to the electronics unit that is electrically coupled to the electrochemical sensor, such that, the electronics unit is operable to obtain the extracted energy as electrical energy from the biofuel cell and to supply the electrical energy to the electrochemical sensor of the multimodal sensor device.

21. A method to simultaneously monitor an electrochemical parameter and an electrophysiological parameter of a user, comprising:

detecting, at electrodes of an electrochemical sensor disposed on a flexible substrate adhered to skin of the user, a first electrical signal produced as a result of a redox reaction involving an analyte in a fluid of the user and a chemical substance coupled to an electrode of the electrochemical sensor;
detecting, at electrodes of an electrophysiological sensor disposed on the flexible substrate adhered to the skin of the user, a second electrical signal associated with an electrophysiological signal of the user,
wherein the detecting the first electrical signal at the electrodes of the electrochemical sensor occurs at the same time as the detecting the second electrical signal at the electrodes of the electrophysiological sensor;
amplifying, at an electronics unit, the first electrical signal detected by the electrochemical sensor and the second electrical signal detected by the electrophysiological sensor; and
wirelessly transmitting, at the electronics unit, the first electrical signals and second electrical signal to an external device.

22. The method of claim 21, further comprising:
processing the first electrical signal and second electrical signal as digital data, and a memory to store or buffer the digital data.

23. The method of claim 21, further comprising:
extracting electrical energy, at anode and cathode electrodes of a biofuel cell disposed on the flexible substrate, from a fuel substance present in the fluid by converting the fuel substance to a first product in an oxidative process that releases electrons captured at the anode and reducing an oxygenated substance in the fluid to a second product in a chemical reduction process in which the second product gains electrons at the cathode;
obtaining, at the electronics unit, the extracted electrical energy; and
supplying, by the electronics unit, the extracted electrical energy to the electrochemical sensor.

* * * * *